US011890590B2

(12) United States Patent
Martin et al.

(10) Patent No.: US 11,890,590 B2
(45) Date of Patent: Feb. 6, 2024

(54) COLORED ORGANIC/INORGANIC HYBRID MATERIALS AND METHOD FOR PREPARING SAME

(71) Applicants: CENTRE NATIONAL DE LA RECHERCHE SCIENTIFIQUE, Paris (FR); UNIVERSITE PAUL SABATIER TOULOUSE III, Toulouse (FR)

(72) Inventors: François Martin, Saint Foy d'Aigrefeuille (FR); Christophe Le Roux, Avignonet-Lauragais (FR); Pierre Micoud, Peyssies France (FR); Suzanne Fery-Forgues, Monteils (FR); Cyril Aymonier, Begles (FR); Mathilde Poirier, Valence (FR)

(73) Assignees: CENTRE NATIONAL DE LA RECHERCHE SCIENTIFIQUE, Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 1043 days.

(21) Appl. No.: 16/480,940

(22) PCT Filed: Jan. 24, 2018

(86) PCT No.: PCT/EP2018/051728
§ 371 (c)(1),
(2) Date: Jul. 25, 2019

(87) PCT Pub. No.: WO2018/138148
PCT Pub. Date: Aug. 2, 2018

(65) Prior Publication Data
US 2019/0388869 A1 Dec. 26, 2019

(30) Foreign Application Priority Data

Jan. 25, 2017 (FR) ...................... 17 50613

(51) Int. Cl.
*B01J 20/12* (2006.01)
*A61K 33/00* (2006.01)
*B01J 20/10* (2006.01)
*B01J 20/28* (2006.01)

(52) U.S. Cl.
CPC ............. *B01J 20/12* (2013.01); *A61K 33/00* (2013.01); *B01J 20/10* (2013.01); *B01J 20/28007* (2013.01); *B01J 20/28016* (2013.01)

(58) Field of Classification Search
CPC ...... B01J 20/12; B01J 20/10; B01J 20/28007; B01J 20/28016; B01J 13/04; A61K 33/00; A61P 39/00
USPC ....................................... 502/80
See application file for complete search history.

(56) References Cited

U.S. PATENT DOCUMENTS

2015/0240083 A1* 8/2015 Martin ................ C01B 33/38
106/415
2016/0137849 A1 5/2016 Lr Roux et al.

FOREIGN PATENT DOCUMENTS

| FR | 2 792 322 | 10/2000 |
| FR | 3 007 752 | 1/2015 |
| WO | WO 2014/049250 | 4/2014 |
| WO | WO 2014/202920 | 12/2014 |
| WO | WO 2014/207397 | 12/2014 |
| WO | WO 2016/083404 | 6/2016 |
| WO | WO 2016/083418 | 6/2016 |

OTHER PUBLICATIONS

FDA: U.S. Food and Drug Administration. Nanotechnology. 2016. Available online: http://www.fda.gov/Cosmetics/Science Research/Nanotech/default.htm.*
Machine Translation of FR 2 792 322, Oct. 20, 2000.*
International Search Report, PCT/EP2018/051728, dated May 15, 2018.
Yufeng Chen et al: "Structure and photoluminescence of amorphous silicate composites containing ZnO particles synthesized from layered sodium silicate", Journal of Non-Crystalline Solids, vol. 358. No. 15, Jun. 2, 2012 (Jun. 2, 2012), pp. 1772-1777. XP028498083, ISSN: 0022-3093, DOi: 10.1016/J.JNONCRYSOL.2012.05.013 [retrieved on May 18, 2012] the whole document.
Figueiredo Bruno R et al: "Photoluminescent porous and layered lanthanide silicates: A review", Microporous and Mesoporous Materials, vol. 234. Jul. 5, 2016 (Jul. 5, 2016). pp. 73-97, XP029706155 ISSN: 1387-1811. 001: 10.1016/J.MICROMESO.2016.07.004 the whole document.
Martinez et al., "Characterization of Supported Solid Thin Films of Laponite Clay. Intercalation of Rhodamine 6G Laser Dye," Langmuir 2004, 20, 5709-5717.
Rahman et al., "Adsorption characteristics of clay adsorbents—sepiolite, kaolin and synthetic talc—for removal of Reactive Yellow 138:1," Water and Environment Journal, 29 (2015), 375-382.
Reider et al., "Nomenclature of the Micas," The Canadian Mineralogist, vol. 36, pp. 905-912 (1998).

* cited by examiner

*Primary Examiner* — Elizabeth D Wood
(74) *Attorney, Agent, or Firm* — NIXON & VANDERHYE

(57) ABSTRACT

A method for preparing an organic/inorganic hybrid composition including mineral nanoparticles functionalized by at least one molecule chosen from colored charged organic molecules, this method including providing a solution (a) of at least one colored charged organic molecule, providing a suspension (b) of non-swelling phyllosilicate nanoparticles, contacting the solution (a) and the suspension (b), the non-swelling phyllosilicate nanoparticles having a thickness of 1 nm to 100 nm, and a larger dimension of 10 nm to 10 µm. A composition of organic/inorganic hybrid colored nanoparticles obtained by this method is also disclosed.

17 Claims, 4 Drawing Sheets

COLORED ORGANIC/INORGANIC HYBRID MATERIALS AND METHOD FOR PREPARING SAME

Figure 1:
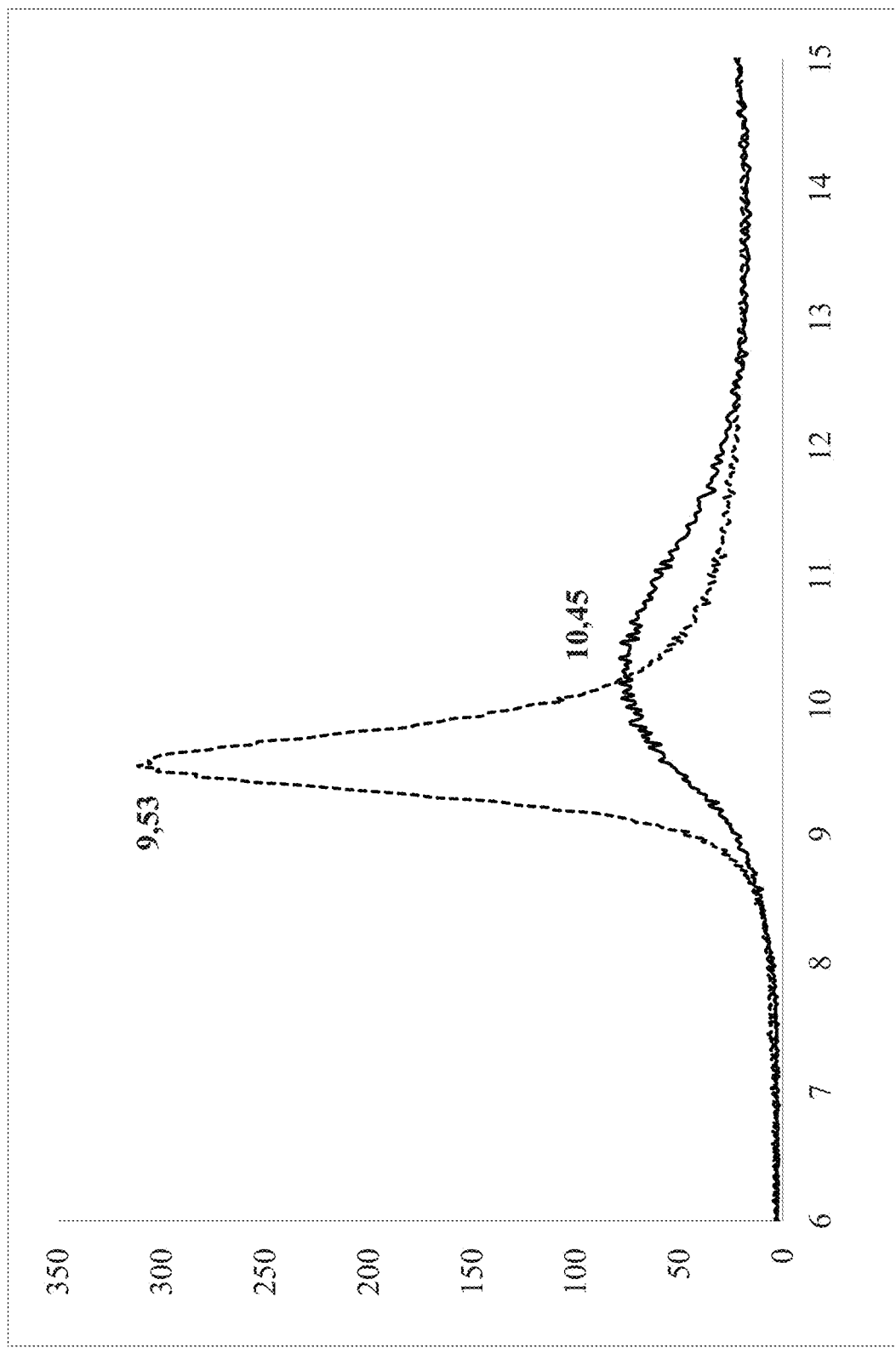

The present invention relates to non-swelling synthetic nano-scale inorganic fillers of phyllosilicates (lamellar silicates) type such as, for example, talc, mica, kaolinite, on which charged organic photoluminescent compounds are adsorbed. The invention also relates to a method for the preparation of these fillers and their uses.

PRIOR ART

Visible colored organic compounds are known for many applications, including marking, coloring, dyeing and the detection of the materials with which they are associated. These may be materials such as polymers, mineral particles, glasses, etc. Some colored materials may also be used in the cosmetic field, and may have both coloring and skincare properties. such as anthocyanins which are known for their role as antioxidants. Thus anthocyanins may be used in cosmetics to prevent or delay the appearance of signs of aging. Applications of such materials are also known in the fields of catalysis or papermaking.

However, some colored organic compounds may be degraded under the conditions in which they are implemented and their properties reduced. Coloring of materials with an organic molecule usually requires the formation of a covalent bond between the compound to be labeled and the colored organic molecule. Such a step is often complicated and expensive, while being likely to modify the behavior of the labeled particle.

While certain natural talcs (steatites) have various colors such as pink, gray or green, when they are in the form of blocks as obtained directly after extraction, their grinding into fine particles (between 2 and 200 µm) leads irreparably to obtaining white to greyish powders, the color of the natural talc being solely due to specific arrangements of talc particles relative to each other. The grinding of such natural talcs thus leads irreparably to a loss of the initial natural pinkish or greenish coloration of the talc.

Mineral particles functionalized by at least one organic group or "organic-inorganic hybrid particles" are of increasing interest in various fields of chemistry, due to their ability to combine certain advantages of organic compounds and inorganic compounds. The creation of strong interactions between organic and inorganic compounds allows a long-term immobilization of organic species on inorganic compounds, providing the organic species with the structural order of the inorganic compounds.

WO2014/049250 describes the combination of silicate mineral particles and coloring molecules to give colored silicate particles. The coloring molecules used in this document are metal cations. Metal salts of transition metals adsorbed on nanometric phyllosilicates give them a coloring, but of lower intensity than with organic dyes.

The metal salts have a different behavior from the organic molecules, their respective properties not being extrapolatable from one family of compounds to another. For example, virtually no adsorption of metal salts on micron sized phyllosilicates is observed, whereas charged organic colored molecules may be partially adsorbed on micron sized phyllosilicates. However, the inventors have surprisingly found a much greater adsorption of colored organic molecules loaded on nanometric phyllosilicates compared to micrometric phyllosilicates.

WO2014/207397 describes a method for the preparation of a composition comprising functionalized mineral particles, in which a phyllosilicate composition comprising mineral particles belonging to the family of lamellar silicates is brought into contact with a solution comprising a water-soluble functionalization agent. selected from the group consisting of oxysilanes and oxygermanes having at least one organic group. This method requires a step of functionalization of the organic group with an oxysilane and/or an oxygen carrier. The hybrid organic-inorganic materials thus obtained do not make it possible to achieve satisfactory grafting rates.

As another alternative to the preparation of organic-inorganic hybrids, there are also known methods of direct synthesis of such materials by sol-gel route. However, these materials have very low crystalline properties and structural properties very far from those of natural or synthetic non-hybrid phyllosilicates. In addition, these sol-gel syntheses can not generally be carried out in an aqueous medium.

Document WO2014/202920 discloses a method for preparing a composition comprising silico/germano-metallic mineral particles functionalized by at least one organic group in which a hydrothermal treatment of a hydrogel precursor of the silico/germano-metallic mineral particles is carried out. The method is characterized in that a hydrogel comprising silico/germano-metallic particles functionalized with at least one organic group is used.

Prior art is known from V. M. Martinez, Langmuir 2004, 20, 5709-5717, hybrid materials based on clay and Rhodamine 60. Unlike the invention, the clays used are swelling materials. The intercalation of Rhodamine 60 or other dyes in swelling clay occurs through an ion exchange mechanism between the hydrated interfoliated cation(s) and the organic molecule.

Compositions comprising synthetic nanotalc and cosmetic active agents, for example UV filters, are known from WO2016/083404. Compositions comprising synthetic nanotalc and electrolytic or polyelectrolytic type cosmetic active ingredients are known from WO2016/083418. However, these active agents are not colored molecules within the meaning of the present invention. Moreover, these documents do not mention the capacity of charged colored molecules to be irreversibly adsorbed on a synthetic nanotalc.

Rahman A. et al., Water and Environment Journal 29 (2015) 375-382 describes the use of natural or synthetic clay particles to remove anionic dyes from a medium. The intended application is the depollution of effluents from textile industries. The materials used are micrometric and have low crystallinity.

The aim of the invention is to provide a method for preparing, in a simple and rapid manner, a composition comprising silicate mineral particles, the particles having coloring properties.

The invention also aims to propose a method for preparing a composition comprising phyllosilicate mineral particles, the particles having coloring properties that are not only modulable according to the desired shade and intensity of the color but also that are durable and stable over time from a composition comprising phyllosilicate mineral particles already synthesized.

Such a composition capable of acting both as a functional mineral filler and as a pigment is of major interest in many fields, such as cosmetics, biology, or mineral fillers for paints, polymers, optical materials, biological marking, as well as inks. Such compositions can also be used as filler in the composition of the papermaking composition.

The invention aims to provide such a method whose implementation is simple and fast, and is compatible with the constraints of an industrial operation.

The invention also aims to propose a method for preparing a wide chemical diversity of compositions comprising mineral particles of structure and properties similar to those of talcs, micas or natural kaolinites, and whose coloring properties may be easily controlled and modified.

The ability of phyllosilicate nanoparticles to irreversibly bind charged colored organic molecules can also be used to extract colored compounds from a medium.

SUMMARY OF THE INVENTION

A first object of the invention relates to a method for preparing an organic/inorganic hybrid composition comprising mineral nanoparticles functionalized by at least one molecule chosen from colored organic charged molecules, this method comprising at least bringing into contact, in a monophasic solvent medium, of at least one colored organic charged molecule and non-swelling phyllosilicate nanoparticles having a thickness of 1 nm to 100 nm, and a largest dimension of 10 nm to 10 μm.

According to a preferred embodiment, the method comprises at least the following steps:
(i) providing a solution (a) of at least one photoluminescent charged organic molecule in at least one solvent,
(ii) providing a suspension (b) of non-swelling phyllosilicate nanoparticles in at least one solvent,
(iii) contacting the solution (a) and the suspension (b).

According to an advantageous embodiment, the method further comprises the following steps:
Elimination of the solvent phase,
Recovery of nanoparticles.

According to a preferred embodiment, the solvent of the solution (a) and the solvent of the suspension (b) are miscible.

The invention also relates to a composition of hybrid nanoparticles comprising at least one non-swelling phyllosilicate and at least one molecule chosen from colored charged organic molecules, said organic molecule being adsorbed on the phyllosilicate, this composition being capable of being obtained by the method according to the invention as described above and in detail below.

According to a preferred embodiment, the non-swelling phyllosilicate nanoparticles have a particle size ranging from 1 nm to 10 μm.

According to a preferred embodiment, the non-swelling phyllosilicate nanoparticles have a thickness of between 1 nm and 100 nm, and a largest dimension of between 10 nm and 10 μm.

According to a preferred embodiment, the non-swelling phyllosilicate are chosen from talc, mica, kaolinites and mixtures thereof.

According to a preferred embodiment, the non-swelling phyllosilicates have the following chemical formula:

$$(Si_xGe(1-x))_4M_3O_{10}(OH)_2, \quad \text{(I) in which:}$$

x is a real number of the interval [0; 1],
M denotes at least one divalent metal having the formula $Mg_{y1}CO_{y2}Zn_{y3}CU_{y4}Mn_{y5}Fe_{y6}Ni_{y7}Cr_{y8}$; each index yi representing a real number of the interval [0; 1], and such that $\Sigma_{i=1}^{8}yi=1$.

According to another preferred embodiment, the non-swelling phyllosilicates have the following chemical formula:

$$(Aly'M'(1-y'))_2(Six'Ge(1-x'))_2O_5(OH)_4, \quad \text{(II) in which:}$$

M' denotes at least one trivalent metal chosen from the group consisting of gallium and rare earths,
y' is a real number of the interval [0; 1],
x' is a real number of the interval [0; 1], According to yet another preferred embodiment, the non-swelling phyllosilicates have the following chemical formula:

$$At(Six''Ge(1-x''))_4M''_kO_{10}(OH)_2, \quad \text{(III) in which:}$$

A denotes at least one monovalent cation of a metal element having the formula $Li_{w1}Na_{w2}K_{w3}Rb_{w4}Cs_{w5}$, each wi representing a real number of the interval [0; 1] such that $\Sigma_{i=1}^{5}wi=1$.
x" is a real number of the interval [0; 1],
M" denotes at least one divalent metal having the formula $Mg_{j1}CO_{j2}Zn_{j3}CU_{j4}Mn_{j5}Fe_{j6}Ni_{j7}Cr_{j8}$; each index ji representing a real number of the interval [0; 1], and such that $\Sigma_{i=1}^{8}ji=1$,
k is a real number in the range [2.50; 2.85],
t+2 k is a real number of the interval [5.3, 6.0].

According to a preferred embodiment, the non-swelling phyllosilicates are formed of a stack of elementary sheets of 2:1 phyllosilicate type and correspond to the following chemical formula:

$$(Si_xGe(1-x))_4M_3O_{10}(OH)_2, \quad \text{(I) in which:}$$

x is a real number of the interval [0; 1],
M denotes at least one divalent metal having the formula $Mg_{y1}CO_{y2}Zn_{y3}CU_{y4}Mn_{y5}Fe_{y6}Ni_{y7}Cr_{y8}$; each index yi representing a real number of the interval [0; 1], and such that $\Sigma_{i=1}^{8}yi=1$.

According to another preferred embodiment, the non-swelling phyllosilicates are formed of a stack of phyllosilicate elementary sheets: 1 and correspond to the following chemical formula:

$$(Aly'M'(1-y'))_2(Six'Ge(1-x'))_2O_5(OH)_4, \quad \text{(II) in which:}$$

M' denotes at least one trivalent metal chosen from the group consisting of gallium and rare earths,
y' is a real number of the interval [0; 1],
x' is a real number of the interval [0; 1], According to yet another preferred embodiment, the non-swelling phyllosilicate are formed of a stack of 2:1 phyllosilicate elemental sheets and have the following chemical formula:

$$At(Six''Ge(1-x''))_4M''_kO_{10}(OH)_2, \quad \text{(III) in which:}$$

A denotes at least one monovalent cation of a metal element having the formula $Li_{w1}Na_{w2}K_{w3}Rb_{w4}Cs_{w5}$, each wi representing a real number of the interval [0; 1] such that $\Sigma_{i=1}^{5} wi=1$.
x" is a real number of the interval [0; 1],
M" denotes at least one divalent metal having the formula $Mg_{j1}CO_{j2}Zn_{j3}Cu_{j4}Mn_{j5}Fe_{j6}Ni_{j7}Cr_{j8}$; each index ji representing a real number of the interval [0; 1], and such that $\Sigma_{i=1}^{8}ji=1$,
k is a real number in the range [2.50; 2,85]
t+2 k is a real number of the interval [5.3; 6,0].

According to a still preferred embodiment, the non-swelling phyllosilicates are formed of a stack of elementary sheets:
of phyllosilicate type 2:1 and of chemical formula $Si_4M_3O_{10}(OH)_2$, more particularly of chemical formula $Si_4Mg_3O_{10}(OH)_2$.

According to a still preferred embodiment, the non-swelling phyllosilicates are formed of a stack of elementary sheets:

Phyllosilicate type 1:1 and chemical formula $Al_2Si_2O_5(OH)_4$.

According to a still preferred embodiment, the non-swelling phyllosilicates are formed of a stack of elementary sheets:
of phyllosilicate type 2:1 and of chemical formula $KSi_4Mg_{2.5}O_{10}(OH)_2$ (IIId) or $K_{0.8}Si_4Mg_{2.6}O_{10}(OH)_2$ (IIIf))

According to one embodiment, the colored organic molecule is chosen from those having an absorption in the visible range (wavelength ranging from 380 to 780 nm).

According to one embodiment, the solution (a) further comprises at least one charged photoluminescent organic molecule selected from those having an absorption in the ultraviolet range (wavelength ranging from 200 to 380 nm) or the visible range (length of wave ranging from 380 to 780 nm), and re-emitting the absorbed energy in light form.

According to a still more preferred embodiment, the colored organic molecule is chosen from:
polyphenols, in particular anthocyanins, such as pelargonidine, cyanidine, peonidine, delphinidin, petunidine, malvidine, apigenidine, luteolidine, tricetinidine, 6-hydroxypelargonidine, 6-hydroxy cyanidine, 6-hydroxy delphinidin, europinidine, rosinidine, capensinidine, pulchelidine, hirsutidine, 5-methylcyanidine, fisetinidine, as well as melanins such as eumelanin and pheomelanin, and derivatives thereof, including synthetic analogues, humic acids,
methylene blue or 3,7-bis(dimethylamino)phenothiazin-5-ylium chloride, crystal violet or tris(4-(dimethylamino)phenyl)methylium chloride, congo red or benzidinediazo-bis-1-acid naphthylamine-4-sulfonic acid, porphyrins, in particular porphine, eosin γ or bromofluorescent acid, eosin B or imperial red, thiazole orange or p-tosylate of 1-methyl-4-[(3-methyl-2(3H) benzothiazolylidene)methyl]quinolinium, acid black 1 (CAS 1064-48-8), acid black 2 (CAS 8005-03-6), eriochrome black T or (4Z)-4-[sodium1-hydroxynaphthalen-2-yl-hydrazinylidene]-7-nitro-3-oxo-4-naphthalene-1-sulphonate, patent blue V (CAS 20262-76-4 and 3536-49-0),
an aqueous extract of a colored vegetable fraction, such as an aqueous extract of grapes, elderberries, pomegranates, acai, poppy petals, mauves, peonies or beetroot,
an aqueous extract of a colored animal fraction, for example a cochineal extract,
a product derived from these plant and animal extracts, such as wine,
mixtures of these compounds.

According to a preferred embodiment, the ratio of the organic colored molecule/phyllosilicate is from 0.001% to 10% by weight of carbon relative to the phyllosilicate mass, preferably from 0.01% to 5% by weight of carbon, referred to the phyllosilicate mass.

According to one embodiment, the hybrid nanoparticle composition is a solid composition, for example a powder.

According to this embodiment, preferably the hybrid nanoparticle composition consists essentially of one or more non-swelling phyllosilicates and one or more molecules chosen from colored charged organic molecules.

According to this embodiment, the hybrid nanoparticle composition advantageously consists of one or more non-swelling phyllosilicates and one or more molecules chosen from colored charged organic molecules.

According to another embodiment, the hybrid nanoparticle composition is a fluid composition, such as, for example, a solution, a suspension, a dispersion or a gel.

According to this embodiment, advantageously, the hybrid nanoparticle composition comprises one or more non-swelling phyllosilicates, at least one molecule chosen from colored charged organic molecules and at least one solvent selected from water, organic solvents, and mixtures of water and solvents miscible with water.

According to one embodiment, the hybrid nanoparticle composition consists essentially of one or more non-swelling phyllosilicates, one or more molecules chosen from colored charged organic molecules and at least one solvent selected from water, organic solvents, and mixtures of water and solvents miscible with water.

According to one embodiment, the composition of hybrid nanoparticles consists of one or more non-swelling phyllosilicates, one or more molecules chosen from colored charged organic molecules and a solvent chosen from water, organic solvents, and water mixtures. and solvents miscible with water.

The invention also relates to the use of non-swelling phyllosilicate nanoparticles for extracting an environment from a colored organic charged molecule, it being understood that when said environment is a biological tissue, it is an isolated biological tissue or cultivated.

The invention also relates to non-swelling phyllosilicate nanoparticles for their medical use for extracting a colored organic charged molecule from an individual or animal contaminated with such a molecule.

Another object of the invention relates to a method for extracting a colored organic molecule loaded from an environment in which the colored organic charged molecule is present, this method comprising at least the following steps:
(1) providing a suspension (b) of non-swelling phyllosilicate nanoparticles,
(2) Contacting the suspension (b) and the environment, it being understood that when said environment is a biological tissue, it is an isolated biological tissue or cultivated.

The method of the invention has the advantage of allowing the formation of the composite directly from a colored organic molecule without requiring the functionalization of this molecule or of the phyllosilicate nanoparticle by metal groups or by other binding agents. The formation of the composite is based on the adsorption of the organic molecule loaded on the non-swelling phyllosilicate. This method may be carried out in an aqueous or organic medium. It may be implemented from a composition of mineral nanoparticles with different colored molecules, without it being necessary to form organic/inorganic hybrid precursors prior to the production of the nanoparticles. This way of proceeding gives the method of the invention more flexibility than some previous methods for the preparation of materials of various colors.

Surprisingly, the inventors have observed that non-swelling phyllosilicate particles, of nanometric size, have a great ability to adsorb colored organic molecules insofar as the latter are carrying charges. The very strong adsorption of the colored organic compounds on the nanofillers makes it almost impossible to diffuse the colored molecules into the medium and leads to very stable hybrid compounds. These properties are all the more surprising since, comparatively, phyllosilicates of micro-size show an extremely low adsorption capacity.

The association of charged organic molecules with non-swelling lamellar minerals makes it possible to obtain an organo-mineral hybrid material having selected coloring properties, which can be varied in intensity and in hue.

The non-swelling phyllosilicate nanoparticles used in the method of the invention have an adsorption capacity of charged organic coloring molecules which is much higher than that of natural non-swelling phyllosilicates.

Compared to the swelling phyllosilicates such as certain clays, the non-swelling phyllosilicate nanoparticles used in the method of the invention have a coloration of comparable intensity, with a lesser amount of dye. Also, in the case of expensive dyes, the color rendering may be identical to that of a swelling clay composite, with a much lower raw material cost.

In the case where toxic colored markers are used in the laboratory, awkward handling can lead to contact with the skin or mucous membranes of the manipulator, or even ingestion of the product. A composition based on phyllosilicate nanoparticles can, by its very strong adsorption capacity of such molecules, be used to irreversibly fix such toxic compounds and facilitate their elimination.

In the present description, the expression "between X and Y" is understood to include the limits, i.e. the parameter may take the values X, Y or any value between X and Y.

The expression "consists essentially of" followed by one or more characteristics means that, in addition to the components or steps explicitly listed, may be included in the method or material of the invention, components or steps that do not significantly modify the properties and characteristics of the invention.

Throughout the description, the terms "composite" and "hybrid" are used interchangeably to designate a mixed organic/inorganic material.

Throughout the description, the term "phyllomineral particle" means any mineral particle having a crystalline structure comprising at least one tetrahedral layer and at least one octahedral layer. It may be for example phyllosilicates.

When it is indicated that two solvents are miscible, it is meant that they are miscible in all proportions when they are at room temperature, that is to say at a temperature ranging from 20° C. to 25° C.

DETAILED DESCRIPTION

The inventors have surprisingly found that a method according to the invention makes it possible to color a non-swelling phyllosilicate composition in a simple, rapid but nevertheless durable manner. Thus, a simple contacting of said phyllosilicate composition in a coloring solution comprising ions of at least one element selected from charged colored organic molecules, makes it possible to obtain a composition comprising colored phyllosilicate mineral particles. Such a method according to the invention also makes it possible to obtain a phyllosilicate mineral particle composition having desired pigment-like coloring properties, which are easily adjustable in intensity and shade, which make it possible to cover all the colors of the pigment. visible spectrum, and then remain stable over time.

The surprising nature of this coloration lies notably in the fact that with different particles of the silicate mineral particles according to the invention, of micrometric size, a very weak coloration of the particles is obtained. The durability and irreversibility of such a coloring step remain to this day still unexplained, as well as the ease with which this coloring is made possible.

Phyllosilicate Nanoparticles

Phyllosilicates are lamellar minerals widely distributed on the surface of the Earth. These minerals consist of a stack of layers along the crystallographic axis c* and are known for some for their high adsorption capacity.

Phyllosilicates are constituted by a regular stack of elementary sheets of crystalline structure, the number of which varies from a few units to several thousand units. Among the phyllosilicates (lamellar silicates), the group including talc, mica and smectites is characterized in that each elemental sheet is constituted by the association of two layers of tetrahedrons located on either side of a layer of octahedra. This group corresponds to phyllosilicates 2:1. In view of their structure, phyllosilicates 2:1 are also described as T.O.T. (Tetrahedron-octahedron-tetrahedron). Natural talc, which is a hydroxylated magnesium silicate of formula $Si_4Mg_3O_{10}(OH)_2$, belongs to the family of phyllosilicates.

The octahedral layer of phyllosilicates 2:1 is formed of two planes of O 2 and OK ions (in the molar ratio $O^2/OH$ of 2/1). On either side of this middle layer come two-dimensional networks of tetrahedra, one of whose vertices is occupied by an oxygen of the octahedral layer, while the other three are by substantially coplanar oxygens.

Some phyllosilicates, such as smectites, are characterized by the presence of interfoliary spaces between the elemental layers that contain water and cations and form a swelling phase of the mineral. Smectites are therefore described as T.O.T. swelling. This exchangeable, swelling phase is not present in the non-swelling phyllosilicates used in the present invention.

The micas are characterized in particular by the presence of interfoliary cations in spaces, called interfoliary spaces, located between the elementary sheets. Unlike smectites, micas are said to be non-swelling and are characterized by the absence of water molecules in interfoliary spaces, the water molecules notably implying a property of swelling of the mineral.

As defined in the scientific publication entitled" Nomenclature of Micas" by Rieder et al. (The Canadian Mineralogist, 1998, Vol 36, pp 41-48), the simplified formula for micas is:

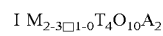

I $M_{2-3}\square_{1-0}T_4O_{10}A_2$ in which I denotes an interfolary cation (generally K, Na or Ca for example); M is generally selected from Li, Fe, Mg, Al or Ti; $\square$ represents a vacancy, T is generally selected from Al, Fe (trivalent) or Si, and A is generally selected from F and OH in particular.

Micas therefore generally comprise many chemical elements including silicon, aluminum or iron in tetrahedral sites (T in the general formula of Rieder et al.) And lithium, iron, magnesium, potassium aluminum or titanium in the octahedral sites (M in the general formula of Rieder et al).

The micas are also characterized by an X-ray diffraction line characteristic of a (001) plane located at a distance between 9.80 Å and 10.30 Å.

Kaolinites also belong to the family of phyllosilicates. Among the phyllosilicates, the group comprising in particular kaolinite and serpentine is characterized in that each elemental sheet is constituted by the combination of a layer of tetrahedra and a layer of octahedra. The octahedral layer of the phyllosilicates 1:1 is formed of a plane of $O^-$ and $OH^-$ ions (in the molar ratio $O^{2-}/OH$ of 1/1). Each tetrahedral layer forms a two-dimensional network of tetrahedra, one of whose vertices is occupied by an oxygen of the octahedral layer, while the other three are formed by substantially coplanar oxygens. This group corresponds to phyllosilicates 1:1. Given their structure, phyllosilicates 1:1 are also called T.O. type (tetrahedron-octahedron). Like talc and mica, kaolinites are said to be non-swelling and are characterized by the absence of water molecules and cations in the interfoliary spaces (spaces between each elementary sheet).

According to the invention, the term "phyllosilicate particles" means particles belonging to the group formed by lamellar silicates, lamellar germanates, lamellar germanosilicates and mixtures thereof.

Advantageously, the invention relates to lamellar silicates.

The phyllosilicates used in the present invention belong to the category of non-swelling phyllosilicates.

In the present invention, the term "non-swelling" refers to any phyllosilicate whose diffraction line (001) is not affected by treatment by contact with ethylene glycol or glycol. that is, the interatomic distance corresponding to the (X-ray) diffraction line (001) does not increase after being contacted with ethylene glycol or glycol. Phyllosilicates 2/1, with the exception of smectites, are non-swelling, it is for example talc or other phyllosilicates belonging to the group of micas such as muscovite. Kaolinites also belong to the category of non-swelling phyllosilicates.

In particular, the composition of phyllosilicate nanoparticles that can be used in the method of the invention does not exhibit, in X-ray diffraction, a diffraction line characteristic of a plane located at a distance of between 12.00 Å and 18.00. Å, characteristic of a swelling phase.

Advantageously, the non-swelling phyllosilicates used in the present invention are selected from synthetic talc, synthetic mica, synthetic kaolinites and mixtures thereof.

Advantageously, the non-swelling phyllosilicates used in the present invention have one of the following chemical formulas:

$$(Si_xGe(1-x))_4M_3O_{10}(OH)_2, \quad \text{(I)}$$ in which:

x is a real number of the interval [0; 1],

M denotes at least one divalent metal having the formula $Mg_{y1}Co_{y2}Zn_{y3}Cu_{y4}Mn_{y5}Fe_{y6}Ni_{y7}Cr_{y8}$; each index yi representing a real number of the interval [0; 1], and such that $\Sigma_{i=1}^{8} yi=1$, or $$(Al y'M'(1-y'))_2(Si x'Ge(1-x'))_2O_5(OH)_4, \quad \text{(II)}$$ in which:

M' denotes at least one trivalent metal chosen from the group consisting of gallium and rare earths, y' is a real number of the interval [0; 1], x' is a real number of the interval [0; 1], or $$At(Si x''Ge(1-x''))_4M''_kO_{10}(OH)_2, \quad \text{(III)}$$ in which:

A denotes at least one monovalent cation of a metal element having the formula $Li_{w1}Na_{w2}K_{w3}Rb_{w4}Cs_{w5}$, Li denoting lithium, Na denoting sodium, K denoting potassium, Rb denoting rubidium, Cs denoting cesium and each wi representing a real number of the interval [0; 1] such that $\Sigma_{i=1}^{5} wi=1$.

x" is a real number of the interval [0; 1],

M" denotes at least one divalent metal having the formula $Mg_{j1}CO_{j2}Zn_{j3}CU_{j4}Mn_{j5}Fe_{j6}Ni_{j7}Cr_{j8}$; each index ji representing a real number of the interval [0; 1], and such that $\Sigma_{i=1}^{8} ji=1$, k is a real number in the range [2.50; 2.85], t+2 k is a real number of the interval [5.3, 6.0].

Even more advantageously, the non-swelling phyllosilicates used in the present invention have at least:

a phase formed of a stack of elementary sheets of 2:1 phyllosilicate type and of chemical formula $Si_4M_3O_{10}(OH)_2$, in which M has the same definition as above, and more particularly of chemical formula $Si_4Mg_3O_{10}(OH)_2$, or a phase formed of a stack of elementary sheets of phyllosilicate type 1:1 and of chemical formula $Al_2Si_2O_5(OH)_4$.

According to another advantageous variant, when the non-swelling phyllosilicates used in the present invention have at least one phase formed of a stack of elementary sheets of phyllosilicate type 2:1 and of chemical formula (III), at least one of the conditions following is verified:

Advantageously, they are free of at least one element chosen from iron, zinc and manganese. In particular, advantageously, a phyllosilicate used according to the invention is free of iron.

In an advantageous variant of formula (III), t is a real number of the interval [0.8; 1], k is a real number of the interval [2.5; 2.6].

In another advantageous variant of formula (III), formula (III) is such that t+2k=6.

In an advantageous variant of the formula (III), x"=1, the compound (III) does not comprise Ge.

In an advantageous variant of the formula (III), the compound (III) may comprise, in octahedral sites, a divalent metal of formula M".M" may therefore be chosen from the group consisting of magnesium, cobalt and zinc, copper, manganese, iron, nickel and chromium. In a particularly advantageous variant of a compound according to the invention, M" is only magnesium (M"=Mg). In this case, the compound has the following formula (IIIa):

$$At(Si_x,Ge(1-x''))_4Mg_kO_{10}(OH)_2 \quad \text{(IIIa)}$$

In other advantageous variants of a compound (III), M" comprises magnesium and at least one other metal such as Mn or Ni.

In particular, in an alternative embodiment of a compound (III), j3 is different from 1. More particularly, in a variant of a compound (III), said compound is devoid of zinc and is equal to zero.

In particular, in an alternative embodiment of a compound (III), j6 is different from 1. More particularly, in a variant of the compound (III), said compound is free from iron and is zero. In fact, it may be advantageous in some applications to have compounds devoid of iron or whose iron content is limited.

Advantageously and according to the invention, in formula (III), A denotes at least one chemical element selected from the group consisting of lithium (Li), sodium (Na), potassium (K), rubidium (Rb) and cesium (Cs). According to one embodiment, A denotes one or other of the chemical elements chosen from the group consisting of lithium (Li), sodium (Na), potassium (K), rubidium (Rb) and cesium (Cs) (such that w1=1, w2=1, w3=1, w4=1 or w5=1 respectively).

In formula (III), A denotes a metal cation arranged in the inter-plane spaces (between the layers) of said compound, each sheet comprising a succession of a tetrahedral layer, an octahedral layer and then a second tetrahedral layer (either a structure of TOT type, T designating a tetrahedral layer and O designating an octahedral layer). Thus, advantageously, a compound of formula (III) is organized according to a solid structure formed of sheets superimposed on each other and separated from each other by at least one space, called interfoliary space, each cation A being disposed in said spaces interlayer.

In particular, advantageously and according to the invention, A is a non-exchangeable interfolary cation, i.e. that it is stably and durably associated with the structure of synthetic mica. This means in particular that it remains associated with said compound when the compound is suspended in pure water for example, or in water saturated with a cation other than A, such as calcium.

According to a particularly advantageous variant of a compound of formula (III), A denotes potassium. In this case, the compound has the following formula (IIIb):

$$K_t(Si_{x''}Ge_{(1-x'')})_4M''_k O_{10}(OH)_2 \quad (IIIb)$$

According to formula (III), the synthetic mica compound has a stoichiometric coefficient t relative to the stoichiometric proportion of A of between 0.30 and 1 (including values), and in particular between 0.80 and 1 (including values). The stoichiometric coefficient t is related to the stoichiometric proportion of metal M'' whose stoichiometric coefficient is k.

In an advantageous variant of a compound of formula (III), said compound is such that t=1 and k=2.5 and has the following formula (III):

$$A(Si_{x''}Ge_{(1-x'')})_4M''_{2.5}O_{10}(OH)_2 \quad (IIIc)$$

When, in the above formula (IIIc), A is potassium, no germanium is substituted for silicon and M'' is magnesium, the compound according to the invention has the following formula (IIId):

$$K\,Si_4Mg_{2.5}O_{10}(OH)_2 \quad (IIId)$$

In another advantageous variant of a compound of formula (III), said compound is such that t=0.8 and k=2.6 and has the following formula (III):

$$A_{0.8}(Si_x\text{—}Ge_{1-x''})_4M''_{2.6}O_{10}(OH)_2 \quad (IIIe)$$

When, in the formula (III) above, A is potassium, no germanium is substituted for silicon and M'' is magnesium, the compound according to the invention has the following formula (IIIf):

$$K_{0.8}Si_4Mg_{2.6}O_{10}(OH)_2 \quad (IIIf)$$

It should be noted that a compound of formula (III) is free of aluminum and fluorine. In particular, advantageously, the phyllosilicate composition is also free of at least one element chosen from aluminum and fluorine. Such compositions may be particularly advantageous in certain applications, for example cosmetic applications (in particular with regard to aluminum).

The non-swelling phyllosilicates used in the method of the invention are implemented in the form of nanoparticles. Advantageously, nanoparticles of dimension ranging from 1 nm to 10 µm are used. Preferably, the phyllosilicate nanoparticles that can be used in the invention have a thickness of between 1 nm and 100 nm and a largest dimension of between 10 nm and 10 µm, the thickness and the largest dimension being evaluated by electron microscopy.

In the present invention, the term "thickness" of the silicate mineral particles the smallest dimension of said particles, the size of said particles in the direction c* of the crystalline lattice of said silicate mineral particles.

In the present invention, the term "largest dimension" refers to silicate mineral particles, the largest dimension of said particles in the plane (a, b) of the crystalline lattice of said silicate mineral particles.

The thickness and the largest dimension of the silicate mineral particles are measured by observation by scanning electron microscopy (SEM) or by transmission electron microscopy (TEM) according to methods which are exposed in the experimental part.

Advantageously and according to the invention, when the particles of formula (I) are used, they have a thickness of between 1 nm and 100 nm, in particular between 5 nm and 50 nm, and a largest dimension between 20 nm and 10 µm.

Advantageously, when using nanoparticles of formula (II), they have an average size of between 20 nm and 600 nm, as observed by electron microscopy.

Advantageously and according to the invention, said synthetic mineral particles of formula (II) have a thickness of between 1 nm and 50 nm, in particular between 2 nm and 30 nm, for example of the order of 10 nm.

Advantageously and according to the invention, the largest dimension of the nanoparticles of formula (II) is between 10 nm and 600 nm, in particular between 20 nm and 500 nm and more particularly between 20 nm and 300 nm.

Advantageously, when nanoparticles of formula (III) are used, they have an average size of less than 500 nm, in particular an average size of between 10 nm and 400 nm (for example as observed by electron microscopy).

The phyllosilicate particles of the invention when mined in the presence of a charged organic dye make it possible to form a hybrid phyllosilicate/organic dye material having an intense coloration.

The inventors have found that the size of the silicate mineral particles is a primordial factor to allow such a coloration. Thus, the inventors have observed that when a method according to the invention is applied to particles of natural talc having a thickness greater than 200 nm, the thickness of the finest natural talc being between 200 nm and 300 nm, only a very low intensity coloration is obtained.

The non-swelling phyllosilicate nanoparticles that can be used in the method of the invention can be obtained as follows:

Method for preparing a phyllosilicate chosen from talc:

In the case of synthetic talc, it is possible to proceed according to the methods described in applications WO2013/004979 and WO2015/159006.

The application WO2013/004979 describes a method for preparing a composition comprising synthetic mineral particles, in which a hydrogel precursor of said synthetic mineral particles is prepared by a co-precipitation reaction between:

at least one compound comprising silicon, and
at least one compound comprising at least one metal element, said co-precipitation reaction taking place in the presence of at least one carboxylate salt of formula $R_2$—COOM'' in which M'' denotes a metal selected from the group consisting of Na and K, and $R_2$ is chosen from H and alkyl groups containing less than 5 carbon atoms.

As a compound comprising at least one metallic element, it is possible to use any metal compound adapted to react in said reaction of co-precipitation of said hydrogel precursor of said synthetic mineral particles.

Advantageously, said compound comprising at least one metal element is a dicarboxylate salt of formula M ($R_1$—COO)$_2$ in which:

$R_1$ is chosen from H and the alkyl groups comprising less than 5 carbon atoms and, M denotes at least one divalent metal having the formula $Mg_{y1}Co_{y2}Zn_{y3}Cu_{y4}Mn_{y5}Fe_{y6}Ni_{y7}Cr_{y8}$; each index yi representing a real number of the interval [0; 1], and such that $\Sigma_{i=1}^{8} yi=1$.

The hydrogel is then subjected to any suitable treatment to obtain said synthetic phyllosilicate mineral particles, for example a batch type hydrothermal treatment. For example, the hydrogel is then subjected to a hydrothermal treatment at a temperature between 150° C. and 400° C. to obtain said phyllosilicate particles.

The groups $R_1$ and $R_2$ may be the same or different, they may be selected from the group consisting of $CH_3$—, $CH_3$—$CH_2$— and $CH_3$—$CH_2$—$CH_2$—.

Advantageously, the compound comprising silicon comprises any compound comprising at least one silicon atom adapted to react in said co-precipitation reaction of said hydrogel precursor of said synthetic mineral particles. In particular, said compound comprising silicon is chosen from the group consisting of sodium silicates and silicas (silicon dioxides).

Advantageously, sodium metasilicate is used as a compound comprising silicon. Advantageously, said hydro gel precursor of said synthetic mineral particles is a silico/germano-metallic hydrogel, of formula $(Si_xGe_{(1-x)})_4M_3O_{11}$, $n'H_2O$:

x being a real number of the interval [0; 1], n' being relative to a number of molecule(s) of water associated (s) with said silico/germano-metallic hydrogel. Preferably, said silico/germanometallic hydrogel has the formula $Si_4M_3O_{11}$, $n^1H_2O$. In this case, said silico/germano-metallic hydrogel of formula $Si_4M_3O_{11}$, $n^1H_2O$ is a silico-metallic hydrogel.

The phyllosilicate mineral particles have at least one non-swelling phase formed of a stack of 2:1 phyllosilicate elemental sheets and of chemical formula $(Si_xGe(1-x))_4M_3O_{10}(OH)_2$. In particular, in a particularly advantageous embodiment of a method according to the invention, said non-swelling phase may be formed of a stack of elementary sheets of 2:1 phyllosilicate type and of chemical formula $Si_4M_3O_{10}(OH)_2$, and more particularly of chemical formula $Si_4Mg_3O_{10}(OH)_2$ (M then denoting magnesium).

At the end of the hydrothermal treatment, a composition is obtained in the form of a colloidal solution containing phyllosilicate mineral particles having at least one non-swelling phase.

At the end of the hydrothermal treatment, a colloidal composition comprising synthetic mineral particles in suspension in an aqueous solution of carboxylate salt(s) is recovered. Said colloidal composition may then be subjected to a drying step, after a possible washing step with water so as to eliminate at least partly said carboxylate salt(s). Such a washing step comprises at least one washing/centrifugation cycle of said colloidal composition.

Said composition comprising synthetic mineral particles obtained by a method according to the invention can be dried by any powder drying technique. Advantageously, following said hydrothermal treatment, said synthetic mineral particles obtained by lyophilization are dried. The drying may also be carried out by means of an oven, for example at a temperature between 60° C. and 130° C., for 1 hour to 48 hours, under microwave irradiation, or else by atomization.

In addition, it is possible to subject the composition comprising synthetic mineral particles obtained after hydrothermal treatment to an anhydrous heat treatment, in air, at a temperature above 350° C. and below the degradation temperature of the synthetic mineral particles. Advantageously, a composition comprising synthetic mineral particles obtained after hydrothermal treatment is subjected to an anhydrous heat treatment, at a temperature of between 350° C. and 850° C. in particular between 400° C. and 750° C. and in particular between 450° C. and 600° C., for example for a period of between 30 minutes and 24 hours.

Advantageously, after said hydrothermal treatment, the composition comprising synthetic mineral particles is subjected to an anhydrous heat treatment. Such a heat treatment or "annealing" allows a further increase in the crystallinity of the particles obtained.

According to this variant, the method of the invention provides phyllosilicate nanoparticles characterized in that they exhibit, in X-ray diffraction, the following characteristic diffraction lines:

a plane (001) located at a distance of between 9.40 Å and 9.90 Å;

a plane (002) located at a distance of between 4.60 Å and 4.80 Å;

a plane (003) located at a distance of between 3.10 Å and 3.20 Å;

a plane (060) located at a distance of between 1.51 Å and 1.53 Å, the intensity of the diffraction line characteristic of a plane (002) being greater than the intensity of the signal corresponding to a plane (020) located at a distance between 4.40 Å and 4.60 Å, and ratio between the intensity of the diffraction line characteristic of a plane (001) and the intensity of the diffraction line characteristic of a plane (003) being between 0.60 and 1.50.

The application WO2015/159006 describes a method for the preparation of simple and fast phyllosilicate nanoparticles, compatible with an exploitation on an industrial scale, producing phyllomineral synthetic particles of high purity, having a lamellar character, and having a fine particle size and low dispersion, as well as a crystalline structure very close to those of natural phyllominerals, especially natural phyllosilicates, and in particular natural talc. Such nanoparticles can be used in the method of the invention.

The method for preparing phyllosilicate particles is carried out by solvothermal treatment of a reaction medium comprising a liquid medium and containing, in stoichiometric proportions, the constituent chemical elements of said particles: this solvothermal treatment is carried out continuously at a pressure greater than 1 MPa and at a temperature of between 100° C. and 600° C., the reaction medium is circulated continuously in a zone, called a solvothermal treatment zone, of a continuous reactor with a residence time of the reaction medium in the solvothermal treatment zone adapted to obtain continuously, at the outlet of the solvothermal treatment zone, a suspension comprising the phyllosilicate particles.

Preferably, the solvothermal treatment is carried out at a pressure of between 2 MPa and 50 MPa.

The solvothermal treatment may be applied to a precursor gel comprising the stoichiometric proportions of the constituent chemical elements of the phyllosilicate particles, the transformation of this precursor gel producing the phyllomineral particles at the end of the solvothermal treatment.

Advantageously, as a precursor gel, a precursor silico/germano-metallic hydrogel is used, and said solvothermal treatment is carried out in the form of a continuous hydrothermal treatment of this silico/germanometallic precursor hydrogel.

A precursor hydrogel can be obtained as described above according to the method taught by WO2013/004979.

According to this variant, the phyllosilicate particles that can be used in the method of the invention and obtained by the method taught by WO2015/159006, exhibit, in X-ray diffraction, the following characteristic diffraction lines:

a plane (001) located at a distance of between 9.40 Å and 12.50 Å;

a plane (003) located at a distance of between 3.10 Å and 3.30 Å;

a plane (060) located at a distance of between 1.51 Å and 1.53 Å.

More particularly, the phyllosilicate particles obtained by a method taught by WO2015/159006 exhibit, in X-ray diffraction, the following characteristic diffraction lines:
a plane (001) located at a distance of between 9.40 Å and 12.50 Å;
a plane (002) located at a distance of between 4.60 Å and 5.00 Å;
a plane (003) located at a distance of between 3.10 Å and 3.30 Å;
a plane (060) located at a distance of between 1.51 Å and 1.53 Å.

Method for preparing a phyllosilicate of kaolinite type:

According to a second variant, the nanoparticles are synthetic kaolinites and are prepared by a method described in application FR15/59125 in which:
a precursor gel of said synthetic mineral particles of formula (II) is prepared by a co-precipitation reaction between:
at least one salt of a metal selected from the group consisting of aluminum and M', M' being selected from iron, galium and rare earths,
at least one source of at least one chemical element selected from the group consisting of silicon and germanium, said source of said chemical element chosen from the group consisting of silicon and germanium being chosen from the group consisting of potassium metasilicate, sodium metasilicate, potassium metagermanate and sodium metrageenate, the molar proportion (Aly'M'(1-y'))/(Six'Ge(1-x')) during the preparation of said precursor gel being equal to 1,
a solvothermal treatment is carried out of said precursor gel at a temperature of between 250° C. and 600° C. for a duration chosen so as to make it possible to obtain synthetic mineral particles of formula (II).

By bringing into contact the above reagents and respecting the stoichiometric proportions of the compound of formula (II) with regard to the molar ratio between aluminum and/or M' and silicon and/or germanium (Aly'M'(1-y'))/(Six'Ge(1-x')), a precursor gel is obtained which makes it possible, after solvothermal treatment, to obtain synthetic mineral particles of formula (II), which method makes it possible to obtain a synthetic mineral non-swelling It is not necessary to dry the precursor gel before carrying out the solvothermal treatment, but it is not excluded to perform such drying if it is desired to dispose or preserve the precursor gel in the form of a powder. In particular, it is advantageous to carry out the solvothermal treatment of said precursor gel without first drying the prepared precursor gel.

The synthetic mineral particles obtained by the method described above do not swell in the presence of ethylene glycol or glycol. The synthetic kaolinites obtained by this method are therefore non-swelling, like natural kaolinites, and have zero electrical charge.

Kaolinites are also characterized by high thermal stability. The synthetic mineral particles obtained by this method also have a high thermal stability, especially up to 400° C. In particular, advantageously, such a synthetic kaolinite is thermally stable up to 450° C. (especially in air).

Advantageously, the synthetic mineral particles obtained by the method described in application FR15/59125 have, in X-ray diffraction, at least one diffraction line characteristic of a plane (001) located at a distance of between 7.00 Å and 7.30 Å, especially at a distance of between 7.00 Å and 7.20 Å.

The synthetic mineral particles obtained by the method described in application FR15/59125 have, in the mid-infrared, four vibration bands between 3610 $cm^{-1}$ and 3700 $cm^{-1}$, representative of the hydroxyl group extension (—OH) vibrations.

Any reagent containing aluminum, gallium or a metal belonging to the rare earth group, capable of allowing the preparation of synthetic mineral particles according to formula (II) (in particular any reagent capable of being solubilized in a solvent, for example in water or in an alcohol) can be used as a source of aluminum or metal M' in a method described in the application FR15/59125 for the preparation of the compounds of formula (II). In particular, advantageously, said aluminum salt is selected from the group consisting of aluminum sulphate, aluminum nitrate, aluminum chloride and aluminum phosphate.

More particularly, said aluminum salt is selected from the group consisting of aluminum chloride and aluminum nitrate.

In an advantageous variant embodiment of this method for preparing the compounds of formula (II), M' denotes at least one trivalent metal (that is to say having at least one oxidation state of 3) chosen from the group formed of iron, gallium and rare earths. In particular, in an alternative embodiment of this method in which M' comprises iron, said solvothermal treatment is carried out continuously and for a period of less than 12 hours, in particular less than 6 hours.

More particularly, M' denotes at least one metal having the formula:

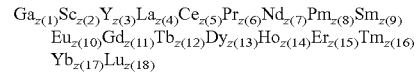

$Ga_{z(1)}Sc_{z(2)}Y_{z(3)}La_{z(4)}Ce_{z(5)}Pr_{z(6)}Nd_{z(7)}Pm_{z(8)}Sm_{z(9)}$
$Eu_{z(10)}Gd_{z(11)}Tb_{z(12)}Dy_{z(13)}Ho_{z(14)}Er_{z(15)}Tm_{z(16)}$
$Yb_{z(17)}Lu_{z(18)}$ in which each z(i) represents a real number of the interval [0; 1], such that $\Sigma_{i=1}^{18} Z(i)=1$ Throughout the text, rare earths are the metals chosen from the group consisting of scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu).

Advantageously, in the method for producing the compounds of formula (II), a base, and in particular a strong base, is added during the coprecipitation reaction of said precursor gel. More particularly, advantageously and according to the invention, during the co-precipitation reaction of said precursor gel, a base selected from the group consisting of NaOH (sodium hydroxide) and KOH (potassium hydroxide) is added.

Said solvothermal treatment is carried out for a time allowing synthetic mineral particles to be obtained according to formula (II). The duration of the solvothermal treatment is chosen as a function of the temperature and the pressure during the solvothermal treatment as well as the conditions under which it is carried out (batch, continuous) and possibly of the nature of the solvent used. In particular, synthetic mineral particles according to formula (II) can be obtained after a few minutes, or even after a few seconds of solvothermal treatment. The duration of the solvothermal treatment is, for example, greater than 10 seconds and less than 6 hours, and for example less than 1 hour in the case of a continuous preparation. In particular, advantageously, said solvothermal treatment is carried out for a period of less than 48 hours, especially less than 24 hours. More particularly, said solvothermal treatment is carried out for a period of less than 20 hours, in particular less than 18 hours and for example less than 12 hours.

The solvothermal treatment may be carried out in a sealed closed reactor (autoclave for example) or continuously. In a particularly advantageous variant, said solvothermal treatment is carried out continuously, in particular by using a continuous reactor. Any known continuous reactor may be used in a method as described above. Thus, advantageously, said continuous reactor is a constant volume continuous reactor. In a particularly advantageous variant of this method, a continuous reactor chosen from the group consisting of piston reactors (or piston-type flow reactors) is used. It may for example be tubular reactors in which the flow of the reaction medium is carried out in a laminar, turbulent or intermediate regime. In addition, it is possible to use any continuous cocurrent or countercurrent reactor with regard to the introduction and bringing into contact of the different compositions and/or liquid media contacted in this method.

The solvothermal treatment of a reaction medium comprising said precursor gel is carried out in a solvothermal treatment zone of the reactor at a temperature adapted to allow said synthetic particles to be obtained, in particular as a function of the pressure and the duration of the solvothermal treatment. Advantageously and according to the invention, said solvothermal treatment is carried out at a temperature of between 280° C. and 450° C. More particularly, advantageously and according to the invention, said solvothermal treatment is carried out at a temperature of between 290° C. and 420° C., in particular between 290° C. and 400° C., and in particular between 295° C. and 375° C.

The solvothermal treatment of a reaction medium comprising said precursor gel is carried out in a solvothermal treatment zone of the reactor at a pressure suitable for obtaining said synthetic particles, depending in particular on the temperature and the duration of the solvothermal treatment. Advantageously, said solvothermal treatment is carried out at a pressure greater than 1 MPa. More particularly, said solvothermal treatment is carried out at a pressure of between 2 MPa and 50 MPa, in particular between 8 MPa and 40 MPa, and in particular between 22 MPa and 30 MPa. This is, in particular, the saturated vapor pressure at the temperature at which the solvothermal treatment is carried out, if the solvent is water. In a particularly advantageous variant of this method, said solvothermal treatment is carried out in an aqueous medium. It is then a hydrothermal treatment. Water may be used as a sole solvent or diluent or mixed with any other fluid.

Advantageously and according to the invention, it is possible to use as chemical formula for said precursor gel, the following chemical formula (IIbis):

$$2(Al y'M'(1-y'))2(Si x'Ge(1-x'))(5-\varepsilon)O(4+2\varepsilon)OH \qquad \text{(IIbis)},$$

in which ε is a real number of the interval [0; 5].

Another chemical formula is sometimes also used to define said precursor gel, it is the following formula: $(Al y'M'(1-y'))_2 (Si x'Ge(1-x'))_2O_7$, or with regard to a precursor gel for the preparation of a synthetic kaolinite with x'=1, y'=1: $Al_2Si_2O_7$.

Method for preparing a phyllosilicate of mica type:

According to a third variant, the nanoparticles are micas and are prepared by a method described in patent application FR15/59129 comprising the following steps:

1/Preparation of a precursor gel of a compound of formula (III)

The precursor gel of a compound of formula (III) may be prepared by a coprecipitation reaction involving, as a reagent, at least one source of silicon and/or at least one source of germanium chosen from the group formed of potassium metasilicate and potassium metagermanate, and at least one metal salt of a divalent metal M", M" denoting at least one divalent metal having the formula $Mg_{j1}Co_{j2}Zn_{j3}Cu_{j4}Mn_{j5}Fe_{j6}Ni_{j7}Cr_{j8}$; each index ji representing a real number of the interval [0; 1], and such that $\Sigma_{i=1}^{8} ji=1$, (Mg denoting magnesium, Co denoting cobalt, Zn denoting zinc, Cu denoting copper, Mn denoting manganese, Fe denoting iron, Ni denoting nickel and Cr denoting chromium) and each ji representing a real number of the interval [0; 1], such that $\Sigma_{i=1}^{8} ji=1$.

This coprecipitation reaction makes it possible to obtain a precursor gel exhibiting the stoichiometry of a synthetic mica corresponding to formula (III).

The precursor gel is prepared by a coprecipitation reaction implemented from:
  an aqueous solution in which at least one metal salt of a divalent metal M" is dissolved, for example an aqueous solution of a metal sulphate (M"SO$_4$),
  a solution of sulfuric acid (H$_2$SO$_4$), and
  an aqueous solution of potassium metasilicate or an aqueous solution of potassium metagermanate, or a mixture of these two solutions in the molar proportions x"/(1-x").

The molar proportion (Six"Ge(1-x"))/M" during the preparation of this precursor gel is in the range [2/1.425; 1.6], and in particular in the range [2/1.3; 1.6].

The preparation of this precursor gel is carried out according to the following protocol:

The solution comprising at least one metal salt is mixed with the sulfuric acid solution and the aqueous solution of potassium meta-silicate and/or potassium metagermanate is then added thereto; the precursor gel is formed instantly.

The suspension obtained comprising the precursor gel may be stirred at room temperature (for example at 22.5° C.) for 5 to 30 minutes and then subjected to several cycles of washing and centrifugation or may be directly subjected to these cycles. washing and centrifugation.

The precursor gel may also be recovered after centrifugation (for example between 3000 and 15000 rpm, for 5 to 60 minutes) and removal of the supernatant (potassium sulfate solution) and washing with demineralized water (for example three washes and successive centrifugations).

The precursor gel washed and separated from the solution comprising potassium is then subjected to a solvothermal treatment as obtained at the end of the last centrifugation or possibly after having been dried (for example in an oven or by lyophilization).

At least one hydroxide of formula AOH is then added to said precursor gel so that the molar proportion A/M" is at least equal to t/k.

A suspension of precursor gel and hydroxyl AOH is thus obtained.

2/—Solventothermal treatment of said precursor gel

The precursor gel as previously obtained (after the addition of the hydroxyl AOH) is subjected to a solvothermal treatment at a temperature of in particular between 300° C. and 600° C.

In a first variant, the solvothermal treatment of the precursor gel is carried out in a closed reactor.

To do this, the precursor gel is placed in a reactor/ autoclave that is placed inside an oven or an oven, at a predetermined reaction temperature (set between 300° C. and 600° C.), during the entire duration of the solvothermal treatment.

In advance, the liquid/solid ratio may be adjusted to a value of between 2 and 80, in particular between 5 and 50 (the quantity of liquid being expressed in cm$^3$, and the amount of solid, in grams, and denoting the amount of gel dry only).

In particular, it is preferable to place the reactor or the autoclave under the conditions of temperature and pressure of the solvothermal treatment less than 6 hours, especially less than 3 hours, and more particularly less than one hour, after adding the hydroxide of formula AOH to the precursor gel.

During the hydrothermal treatment, the precursor gel gradually acquires a gelatinous consistency. The composition obtained at the end of the solvothermal treatment has an observable crystallinity in X-ray diffraction, this crystallinity increasing with the duration of the solvothermal treatment and resulting in the corresponding diffractograms by the rapid appearance of characteristic lines which are refined and' intensify rapidly during treatment.

At the end of this solvothermal treatment, a composition is obtained comprising mineral particles of synthetic mica according to formula (III) in suspension in a solution, in particular an aqueous solution. At the end of this solvothermal treatment, the composition contained in the reactor is recovered by centrifugation (between 3000 and 15000 rpm, for 5 to 60 minutes) and then removal of the supernatant.

The composition comprising mineral particles recovered after the last centrifugation can then be dried:

in an oven at a temperature between 60° C. and 130° C., for 1 to 24 hours, or, by lyophilization, for example in a freeze-dryer of the CHRIST ALPHA® 1-2 LD Plus type, for 48 hours at 72 hours, or by atomization.

In a second variant, the solvothermal treatment of the precursor gel is carried out continuously.

Figure 4:
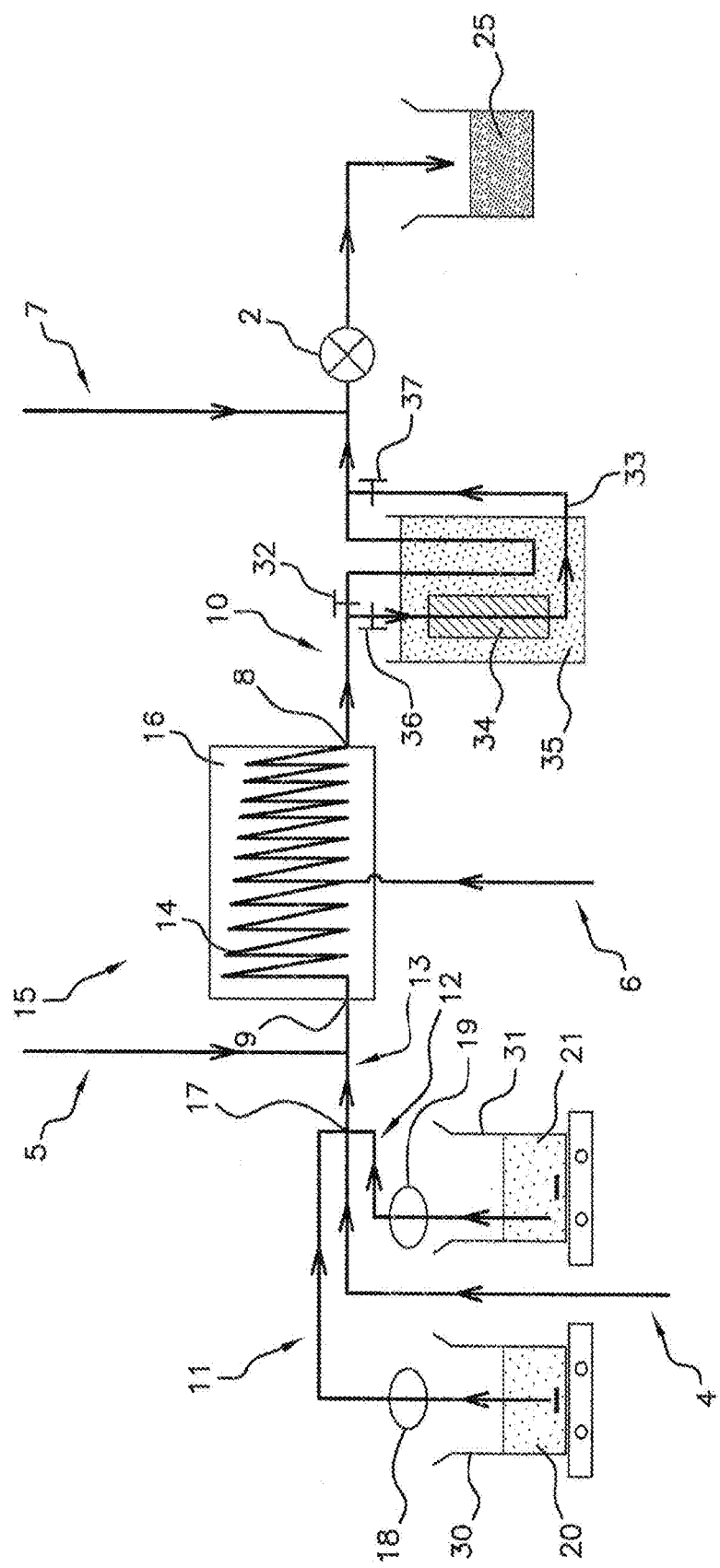

In a method in which the solvothermal treatment is carried out continuously, a reactor 15 for preparing mineral particles of a compound according to the invention is used continuously (as illustrated in FIG. 4) comprising:

a first portion 11 of conduit in which a first aqueous solution 20 comprising the precursor gel is introduced, a second portion 12 of conduit in which a second aqueous solution 21 comprising at least one hydroxide of formula AOH (KOH for example) is introduced, a third portion 13 of conduit disposed after the first conduit portion 11 and the second conduit portion 12 and extending to an inlet 9 of a reaction chamber 16, the first conduit portion 11 and the second portion 12 of conduit joining at a point 17 from which begins the third portion 13 of conduit, a reaction conduit 14 extending from the inlet 9 into the reaction chamber 16, and after the third conduit portion 13.

A peristaltic pump 18 continuously feeds the first portion 11 of conduit with the first aqueous solution 20 contained in a reservoir 30 under stirring. A second peristaltic pump 19 continuously feeds the second portion 12 of conduit with the second aqueous solution 21 contained in a reservoir 31 with stirring.

In order to control the temperature within the reaction conduit 14, the reaction chamber 16 is an oven comprising a heating sleeve comprising ceramic material resistors. The reaction conduit 14 is in the general shape of a coil wound in multiple turns inside the heating sleeve, until it leaves the latter through an outlet 8 constituting the outlet of the reaction chamber 16.

The mixture inside the third portion 13 of the conduit is close to ambient temperature. The third portion 13 of conduit is optional, the point 17 and the input 9 may be combined. In the embodiment as shown in FIG. 4 the third portion 13 of conduit has, for example, a length of between 10 cm and 20 cm.

The total residence time in the device for preparing synthetic mineral particles by a method according to the invention is less than 30 minutes, and in particular less than 15 minutes or even less than 5 minutes or of the order of one minute.

In addition, it is possible to introduce other solutions and, in particular, to adjust the amount of solvent at different levels of the device, for example using inputs 4, 5 located before the solvothermal treatment zone, the inlet 4 being located before the point 17, the inlet 6 being located at the level of the solvothermal treatment zone, the inlet 7 being located after the exit of the solvothermal treatment zone and before the exit of the suspension obtained.

A pressure regulator 2 is disposed downstream of the reaction chamber 16 in connection with a fifth portion 10 of conduit extending from the outlet 8 of the reaction conduit 14 and the reaction chamber 16 to a container 25 in which is recovered a suspension comprising the mineral particles obtained.

The closure of a valve 32 interposed on the fifth portion 10 of conduit makes it possible to circulate the suspension obtained at the outlet 8 of the reaction conduit 14 in a circuit 33 which makes it possible to pass this suspension through a porous sinter 34 adapted to retain the particles and allow their recovery. The porous sinter 34 is immersed in an ice bucket 35 for cooling the suspension leaving the reactor. In this case, valves 36 and 37 disposed on the branch circuit 33 are open. The porous sinter 34 is chosen to retain the synthesized mineral particles by separating them from the liquid medium which carries them. The sintered material is for example made of stainless steel 316L, with a pore size of 50 μm. When the porous sinter is clogged with mineral particles, it suffices to open the valve 32 and to close the valves 36 and 37 to directly recover the suspension in the container 25, this suspension being cooled through the ice container 35, then washed and centrifuged several times to recover the mineral particles which can then be dried, for example in an oven. In another variant (not shown), it is of course also possible to provide several sinters in parallel, which allows the suspension obtained at the outlet of the reaction conduit 14 to be directed to another sinter as soon as the previous is clogged by the particles mineral.

Alternatively, in the case where a solution comprising the precursor gel and the hydroxyl AOH is initially prepared, the same and only portion of the conduit replaces the first conduit portion 11 and the second conduit portion 12. In another variant, it is also possible for the reservoir 30 to contain a solution comprising the precursor gel and for the reservoir 31 to contain the hydroxide AOH.

In each case, it is important to control the dilution of the precursor gel introduced into each portion of conduit and into the reaction conduit 14 so as to allow continuous circulation of the reaction medium in the reaction conduit 14, and in all the conduits supplying said precursor gel composition to the inlet 9 of the reaction chamber 16. The concentration of precursor gel in said precursor gel composition introduced at the inlet of the reaction chamber 16 is advantageously between $10^{-3}$ mol/l and several mol/l, for example of the order of 0.01 mol/L. This concentration is much lower than the concentrations used in the methods for the preparation of synthetic mineral particles such as phyllosilicates of the prior art.

The solvothermal treatment carried out in the reaction conduit 14 is a solvothermal treatment which may, in particular, be carried out under supercritical or subcritical conditions, and in particular under homogeneous subcritical conditions. Thus, it is possible to choose the temperature and the pressure at which this solvothermal treatment is carried out so that the precursor gel composition introduced at the inlet of the reactor, and in particular the solvent(s) it comprises is under supercritical conditions or under homogeneous subcritical conditions, ie above the liquid-gas equilibrium curve of the solvent, and so that the solvent is present at the liquid state and not in the form of a liquid-gas mixture or gas alone.

At the end of this solvothermal treatment, a suspension is obtained comprising inorganic particles in solution, in particular in aqueous solution. At the end of this solvothermal treatment, the suspension obtained is recovered by filtration, for example by means of a ceramic sinter, or else by centrifugation (between 3000 and 15000 rpm, for 5 to 60 minutes) then elimination of the supernatant.

The composition comprising recovered mineral particles may optionally be washed with water, in particular with distilled or osmosis water, for example by carrying out one or two washing/centrifugation cycles.

The composition comprising mineral particles recovered after the last centrifugation can then be dried:
- in an oven at a temperature between 60° C. and 130° C., for 1 to 24 hours, or,
- by lyophilization, for example in a freeze-dryer of the CHRIST ALPHA© 1-2 LD Plus type, for 48 hours at 72 hours,
- by irradiation of microwaves,
- by atomization,
- or by any other powder drying technique.

The mineral particle composition (b) derived from a solvothermal method, advantageously chosen from those described above for each of the 3 variants (talc, kaolinite, mica), may be used in the form of an aqueous suspension directly derived from the solvothermal method, possibly with the addition of one or more cosolvents. The inorganic particles may also be dispersed in an organic solvent, after drying the aqueous phase, for use in the method of the invention. Among the organic solvents that may be used, mention may be made of alcohols or polyols, such as, for example, methanol, ethanol, glycerol or ketones, such as propanone or 2-butanone.

Advantageously, the mineral particle composition (b) is in the form of an aqueous suspension or a hydro-organic suspension comprising as solvent a mixture of water and one or more co-solvents such as alcohols or polyols, such as for example methanol, ethanol, glycerol, ketones such as propanone or 2-butanone.

Even more advantageously, the mineral particle composition (b) that can be used in the method of the invention is an aqueous suspension.

Colorful Charged Organic Molecule

According to the invention, the term "colored molecule" or "molecule of dye" is understood to mean a molecule whose coloration appears and is observable in the visible range (wavelength ranging from 380 to 780 nm).

According to one embodiment, the invention relates to colored molecules chosen from those having an absorption in the visible range (wavelength ranging from 380 to 780 nm).

A colored molecule or dye molecule is any molecule carrying at least one chromophoric moiety having an absorption in the visible range (wavelength ranging from 380 to 780 nm) and whose molar extinction coefficient E is greater than or equal to at 1000 $m^2 \cdot mol^{-1}$, the measurement of the aforementioned molar extinction coefficient being carried out at a temperature of 25° C. in the water, at the wavelength corresponding to the maximum absorbance of the molecule in question and at a temperature of concentration at which the dye is completely soluble in the medium.

Mixtures of colored charged molecules may be used.

By colored organic molecule is meant any molecule which comprises at least one chromophore moiety. The colored molecule may consist entirely of a chromophore moiety.

Advantageously, according to the invention, the chromophore moiety of said molecule contains a sufficient number of conjugated double bonds inducing the chromophore power.

The chromophore moiety of said molecule may also contain heteroatoms (B, N, O, S, P . . . ) inducing or modifying the chromophore power.

Advantageously, according to the invention, the chromophore moiety of said molecule contains a sufficient number of conjugated double bonds to confer a planar or substantially planar character on the chromophore moiety of said molecule.

The colored molecules of the invention advantageously have a planar character, that is to say that at least part of these molecules is flat or substantially planar.

By substantially planar is meant any molecule (or fragment of molecule) for which the deviation of one or more atoms is less than 15 picometers with respect to the mean plane, this deflection being able to be measured by X-ray diffraction (measurement carried out on a monocrystal) or as a result of a molecular modeling in the case where obtaining a single crystal of said molecule could not be possible, using the software i) Accelrys (Discovery Studio Modeling Environment, Release 4.0, San Diego: Accelrys Software Inc., 2013) and ii) Discovery Studio Visualizer 4.0 (DSV).

By molecule comprising a planar part is meant a molecule of which at least 4 atoms connected to each other are placed in the same plane.

By molecule comprising a planar part, advantageously means a molecule of which at least 4 atoms form a structure comprising at least two conjugated multiple bonds.

By multiple bonds is meant bonds selected from double bonds (eg $C=C$ or $N=N$) and triple bonds.

According to one embodiment, the molecule comprising a planar part comprises at least 5 atoms which form a structure comprising at least two conjugated multiple bonds and at least one atom carrying an electron pair.

According to one embodiment, the molecule comprising a planar part comprises at least 6 atoms which form an aromatic ring.

The polycyclic aromatic molecules form a conjugate rrsystem and are planar. The conjugated aromatic heterocyclic molecules generally have a substantially flat structure.

By charged molecule is meant:
i) any molecule (or fragment of molecule) carrying at least one ionizable or ionized function
   in the form of a salt with a metal preferably selected from alkali metals, alkaline earth metals, transition metals and rare earths or mixtures thereof, or
   in the form of an organic salt such as the salts of carboxylic acids or of sulphonic acids;

As well as
ii) any molecule (or fragment of molecule) carrying at least one ionized heteroatom (N, P, S, O), such as for example berberine or methylene blue,
iii) any molecule carrying one or more ionizable or ionized functions and comprising one or more ionized heteroatoms).

By ionizable function is meant a carboxylic acid function, phosphonic acid, a C—SO$_3$H function, as well as phenols. The charged fragment of the molecule may optionally be distinct from the chromophore moiety of said molecule.

Among the visible colored molecules that may be used in the method of the invention, mention may be made of:

Anthocyanins: Anthocyanins belong to the family of polyphenols and are responsible for the coloring of the leaves, stems and roots of many plant species, for example in the case of the violet color of red grapes. Among the anthocyanins are: pelargonidine, cyanidine, peonidine, delphinidine, petunidine, malvidine, apigenidine, luteolidine, tricetinidine, 6-hydroxypelargonidine, 6-hydroxy cyanidine, 6-hydroxy delphinidine, europinidine, rosinidine, capensinidine, pulchelidine, hirsutidine, 5-methylcyanidine, fisetinidine.

These anthocyanin compounds may be used in simple form or in the form of glycosides which are the most frequently encountered form in nature.

Mention may also be made, among the visible colored molecules that may be used in the method of the invention, of melanins (such as eumelanin and pheomelanin), for example those present in the ink of certain cephalopods such as cuttlefish, and its derivatives, including synthetic analogues.

Mention may also be made of humic acids which are derivatives of polyphenols bearing ionizable carboxylic acid functions, and ionized at certain pH. These are high molecular weight, negatively charged polymers resulting from a method of oxidative condensation of phenolic compounds and bound to amino acids, peptides, and polysaccharides.

An example of a structure of the humic acid type is illustrated below:

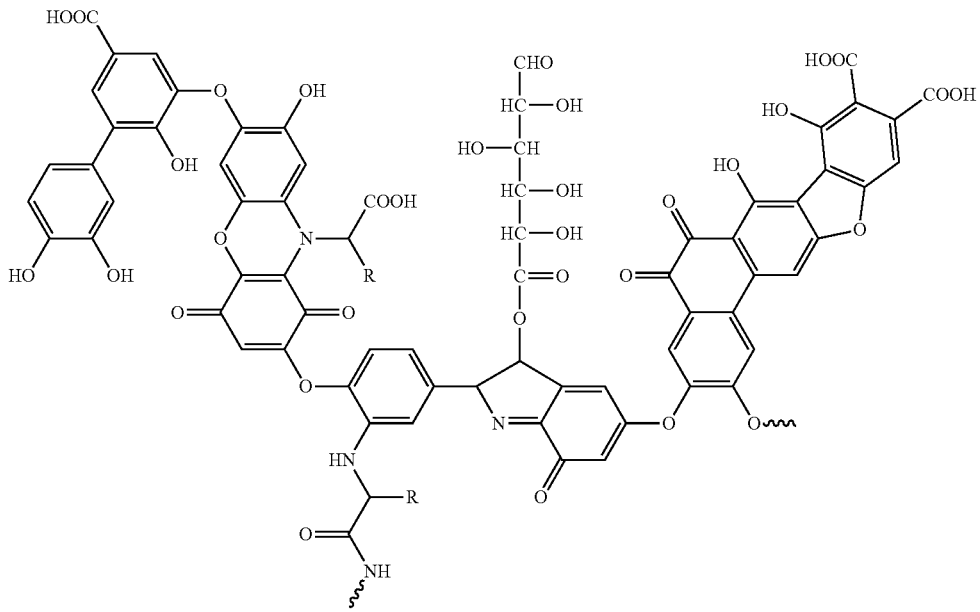

35

Mention may also be made, among the visible colored molecules that may be used in the method of the invention: methylene blue or 3.7bis(dimethylamino)phenothiazine-5-ylium chloride, crystal violet or tris(4(dimethylamino)phenyl chloride)methylium, congo red or benzidinediazo-bis-1-naphthylamine-4-sulphonic acid, porphyrins, in particular porphine, eosin γ or bromofluorescent acid, eosin B or imperial red, thiazole orange or ptosylate of methyl-4-[(3-methyl-2(3H)-benzothiazolylidene)methyl] quinolinium, acid black 1 (CAS 1064-48-8) and acid black 2 (CAS 8005-03-6), Eriochrome black T or (4Z)-4-[(1-hydroxynaphthalen-2-yl -hydrazinylidene)-7-nitro-3-oxonaphthalene-1-sulphonate, blue patent V (CAS 20262-76-4 and 3536-490).

The solution of at least one colored organic molecule that can be used in the method of the invention may consist of a solution of a colored organic molecule alone or of a mixture of colored molecules in a solvent.

According to a variant of the invention, it is possible to use as solution of at least one colored organic charged molecule, an extract, in particular an aqueous extract, of a colored plant fraction, such as for example an aqueous fruit extract. such as grape, elderberry, pomegranate, acai, an aqueous extract of flower petals such as poppies, mauves or peonies, an aqueous extract of vegetables such as beetroot, an aqueous extract of a fraction colored animal, such as for example a cochineal extract . . . , a product derived from these plant and animal extracts, for example wine which is derived from grape juice by alcoholic fermentation.

In the case where a colored animal or plant extract is used, all the colored organic molecules are not necessarily adsorbed on the non-swelling phyllosilicate. In fact, only the charged molecules adsorb on non-swelling phyllosilicate.

It is also possible to use mixtures of charged molecules colored in the visible range, i.e. at a wavelength ranging from 380 to 780 nm, and charged photoluminescent molecules.

By photoluminescent molecule is meant a molecule that absorbs in the ultraviolet range, either at a wavelength ranging from 200 to 380 nm, or in the visible range, or at a wavelength between 380 and 780 nm, and which re-emits the absorbed energy in luminous form.

When a mixture of photoluminescent molecules and colored molecules in the visible range is used, advantageously, the photoluminescent molecule or molecules are charged and part of the structure is planar or substantially planar.

Among the photoluminescent molecules that may be optionally used in the method of the invention, mention may be made of Rhodamine B or [9-(2-carboxyphenyl)-6-diethylamino-3-xanthenylidene]diethylammonium chloride—or any other form of Rhodamine B such as, for example, Rhodamine B perchlorate, ethidium bromide or bromide of 3,8-diamino-1-ethyl-6-phenylphenanthridinium, propidium iodide or 3,8-diamino-5-[3-(diethylmethylammonio) propyl]-6-phenylphenantridinium iodide, the fluorescent brightener compound 220 (CAS 16470-24-9/49549-42-5), the fluorescent compound brightener 251 (CAS 16324-27-9), the fluorescent brightener compound 351 (CAS 27344-41-8), the chloride of 1,1'-diethyl-2,2'-cyanine (CAS: 2402-42-8), 1,1'-diethyl-2,2'-dicarbocyanine iodide (CAS: 14187-31-6).

The colored organic molecule that can be used in the present invention is charged, and the ionic or ionizable function of said molecule may be of a cationic or amicic nature.

Each colored molecule is chosen according to the desired result, in terms of the chemical composition of the colored phyllosilicate composition and in particular the expected coloration.

The solution (a) of at least one colored organic molecule that can be used in the method of the invention may be an aqueous solution, an organic solution or a hydro-organic solution. Among the organic solvents that can be used include methanol, ethanol, glycerol, ketones such as propanone or 2-butanone.

Advantageously, the solution of at least one colored organic molecule that can be used in the method of the invention is an aqueous solution or a hydro-organic solution comprising as solvent a mixture of water and one or more co-solvents such as alcohols or polyols, such as, for example, methanol, ethanol, glycerol, ketones such as propanone or 2-butanone.

Even more advantageously, the solution of at least one colored organic molecule that can be used in the method of the invention is an aqueous solution.

Preparation of the Composition of Colored Nanoparticles

The method of the invention comprises contacting, in a monophasic solvent medium, at least one colored organic charged molecule and non-swelling phyllosilicate nanoparticles having a thickness of 1 nm to 100 nm, and a largest dimension of 10 nm to 10 μm.

According to the invention, the term "monophasic solvent medium" means a solvent or a mixture of solvents miscible with each other. Such solvents form only one phase and do not separate after remaining without stirring. Miscibility is evaluated at room temperature.

Advantageously, a solvent or a mixture of solvents is chosen in which the colored organic charged molecule is soluble and in which the non-swelling phyllosilicate nanoparticles are dispersible.

Advantageously, the solvent chosen is a mixture of water and one or more co-solvents such as alcohols or polyols, for example methanol, ethanol, glycerol or ketones such as propanone or 2-butanone.

Even more advantageously, the solvent used in the method of the invention is water.

According to a first embodiment, the two components: the colored organic charged molecule and the non-swelling phyllosilicate nanoparticles are introduced in powder form in a monophasic solvent medium and dispersed with stirring.

According to a second embodiment, the colored organic charged molecule is implemented in the form of a solution (a) in at least one solvent, the non-swelling phyllosilicate nanoparticles are introduced in powder form into solution (a). The non-swelling phyllosilicate nanoparticles are dispersed in the solution (a) with stirring.

According to a third embodiment, the non-swelling phyllosilicate nanoparticles are used in the form of dispersion (b) in at least one solvent and the colored organic charged molecule is introduced in powder form into dispersion (b).

According to a fourth embodiment, which is the preferred embodiment, the colored organic charged molecule is provided as a solution (a) in at least one solvent, the non-swelling phyllosilicate nanoparticles are provided in the form of a suspension (b) in at least one solvent, then the solution (a) and the suspension (b) are brought into contact.

In a method according to the invention, the duration of step (iii) during which the composition (b) comprising phyllosilicate mineral particles is brought into contact with the solution (a) comprising at least one organic dye-loaded compound, the concentration of each organic dye compound loaded in the dye solution (a) and the temperature at which this step takes place are adapted to allow fixation of the colored organic compound loaded on the phyllosilicate nanoparticles and thus a coloration of the composition of phyllosilicate nanoparticles.

Advantageously and according to the invention, the duration during which the said composition of phyllosilicate nanoparticles (b) is brought into contact with the coloring solution (a) is sufficient to allow the production of colored phyllosilicate particles. A duration of a few seconds may be sufficient in certain cases to obtain good coloration, especially at a sufficient temperature and in the presence of a sufficient concentration of dye compound and optionally by subjecting the mixture comprising the dye solution (a) and the composition of phyllosilicate nanoparticles (b) to ultrasound. Advantageously and according to the invention, the time during which the composition of phyllosilicate nanoparticles (b) is brought into contact with a coloring solution (a) is greater than 2 seconds, especially between 2 seconds and 7 days, in particular between 2 seconds and 24 hours, for example between 5 minutes and 1 hour.

Advantageously, the concentration of the charged colored organic molecule present in the coloring solution (a) is chosen taking into account, in particular, the temperature, the duration of contact with the phyllosilicate nanoparticle composition (b), the nature of the composition of phyllosilicate nanoparticles (b) and the nature of the charged colored organic molecule(s) used, said concentration being chosen to be sufficient to allow the obtaining of the colored phyllosilicate mineral particles. For the implementation of the method of the invention, a solution (a) of at least one colored organic charged molecule of concentration ranging from 0.1 mmol/L to 0.1 mol/L is advantageously used.

The coloring step may be carried out at any temperature at which the coloring solution is in the liquid state and that makes it possible to obtain colored phyllosilicate mineral particles. Advantageously and according to the invention, this coloring step takes place at a temperature of between 5° C. and 100° C. The contacting which takes place in this step of a method according to the invention may for example be carried out at ambient temperature (20° C. to 25° C.) or at a temperature slightly higher than room temperature, in particular between 30° C. and 90° C. and for example between 40° C. and 70° C., depending on the nature of the charged organic color molecule(s) used and phyllosilicate mineral particles to be colored, as well as the shade and intensity of the desired color.

The coloring step may be carried out with or without stirring the coloring solution (a) into which the composition of phyllosilicate mineral particles (b) is added. For example, it is possible to agitate only a few times manually (for example using a metal rod) the coloring solution at the time of adding the phyllosilicate mineral particle composition (b) to the coloring solution (a), then let it rest for the remainder of the coloring step. Advantageously and according to the invention, said phyllosilicate mineral particle composition (b) comprising phyllosilicate mineral particles is brought into contact with the coloring solution (a) with stirring, for example with magnetic stirring using a magnetic stirrer. For example, a slow stirring rate is generally sufficient to allow contacting between the charged organic colorant molecule(s) and the phyllosilicate mineral particle composition (b). allowing the production of colored phyllosilicate mineral particles.

At the end of this step (iii) of coloring of the method according to the invention, the composition comprising colored phyllosilicate mineral particles may be recovered by elimination of the liquid phase. The liquid phase may, for example, be removed after natural decantation of the composition comprising colored phyllosilicate mineral particles or else by centrifugation of the suspension comprising the colored composition obtained. The composition comprising recovered colored phyllosilicate mineral particles may then be rinsed to remove dyes or other non-adsorbed components on phyllosilicate mineral particles. The composition comprising recovered colored phyllosilicate mineral particles may also be stored and used without rinsing. Thus, advantageously, in a method according to the invention, following the coloring step, the colored phyllosilicate mineral particles obtained are rinsed with an organic or aqueous solution devoid of charged colored organic compound.

At the end of this step (iii) of coloring according to the invention, the composition comprising colored phyllosilicate mineral particles may be preserved or used as is, in the form of an aqueous or organic or hydroorganic gel or suspension, or to be dried so as to remove at least partially, the solvent, including water, still present. Advantageously, the colored phyllosilicate mineral particles obtained after the steps (i) to (iii) of the method of the invention are dried, and before or after a possible rinsing. This drying may be carried out by any drying means allowing the elimination of this solvent, in particular of this aqueous phase. The drying may, for example, be carried out directly in an oven (for example at a temperature of the order of 100° C.), by spraying, by drying by microwave irradiation or by lyophilization. Advantageously and according to the invention, the composition comprising colored phyllosilicate mineral particles is dried at a temperature of between 60° C. and 200° C.

In particular, a drying step in an oven at a temperature of the order of 100° C. or 120° C. makes it possible to intensify or shade more or less significantly, depending on the nature of the colored organic compound, in particular the color colored phyllosilicate mineral particles.

In addition, it is possible to repeat at least once the coloring step (iii) in which the phyllosilicate mineral particle composition (b) is brought into contact with the coloring solution (a), or with a solution containing the same colored compound, or with a coloring solution comprising a different colored organic compound. In this way, it is possible to modify or shade the color of such a composition to a greater or lesser extent so as to obtain the desired coloration.

Advantageously, the hybrid nanoparticles of the invention have a ratio of colored organic molecule/phyllosilicate ranging from 0.001% carbon to 10% carbon, preferably from 0.01% carbon to 5% carbon by weight of carbon relative to the phyllosilicate compound mass.

In the case where a visible colored organic compound has been used, the color of a composition comprising colored phyllosilicate mineral particles obtained by a method according to the invention can be visible to the naked eye under any type of illumination. visible light and/or using a detection instrument such as a spectrocolorimeter, the phyllosilicate mineral particles can absorb a portion of the visible spectrum, and reflect another.

In the case where a photoluminescent colored organic compound has been employed, the color of a composition comprising colored phyllosilicate mineral particles obtained by a method according to the invention can be visible to the naked eye under ultraviolet light illumination.

A composition according to the invention has a high chemical stability.

In addition, such compositions may have various colors, depending on the chemical nature of the colored organic compounds attached to the phyllosilicate mineral particles. Compositions comprising colored phyllosilicate mineral particles according to the invention may be of any color, more or less light or dark and more or less intense.

Extraction of Colored Compounds

The ability of phyllosilicate nanoparticles to irreversibly bind charged colored organic molecules may also be used to extract colored compounds, including toxic compounds, from a medium. This may relate, for example, to colored compounds such as ethidium bromide. When such compounds are dispersed in an environment: work table, laboratory equipment, skin, mucous membrane, it is desirable to collect them avoiding greater contamination. It is then possible to use an aqueous dispersion of phyllosilicate nanoparticles, which is placed in contact with the contaminated environment. Charged organic compounds having an affinity for non-swelling phyllosilicates, bind them irreversibly. The solid nature of the nanoparticles allows an easier, more efficient and better safe disposal of these organic compounds.

The nanoparticles can also be used for the treatment of dye-laden aqueous effluents, such as effluents from the chemical, textile and leather industries.

In the case where an individual or an animal has absorbed a colored organic compound, in particular toxic, the absorption by this individual or animal of an aqueous dispersion of nanoparticles of phyllosilicates can be used to neutralize in vivo these toxic molecules.

Among the charged organic molecules concerned by this application mention may in particular be made of ethidium bromide.

FIGURES

FIG. 1: X-ray diffractograms of nanometric talc ( . . . ) and a hybrid product prepared according to the protocol of Example 1 (solid line). The intensity is represented in ordinates as a function of the distance, expressed in Angstrom, on the abscissa.

Figure 2:
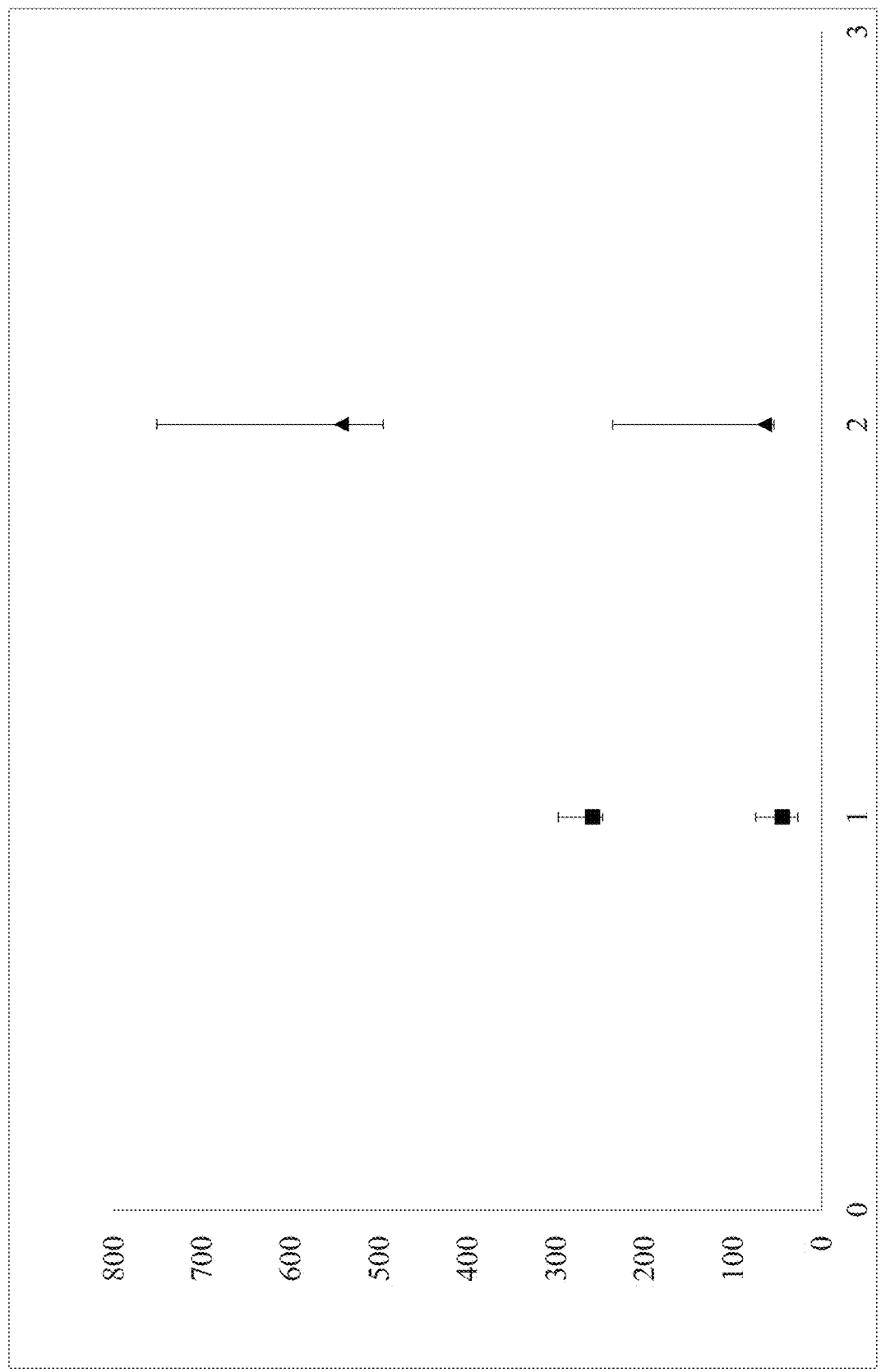

FIG. 2: Granulometry of the synthetic talc (sample 1-■) During the addition of red wine (sample 2-▲) The particle size (in nm) is given in ordinates according to the numbers of samples on the abscissa.

Figure 3:
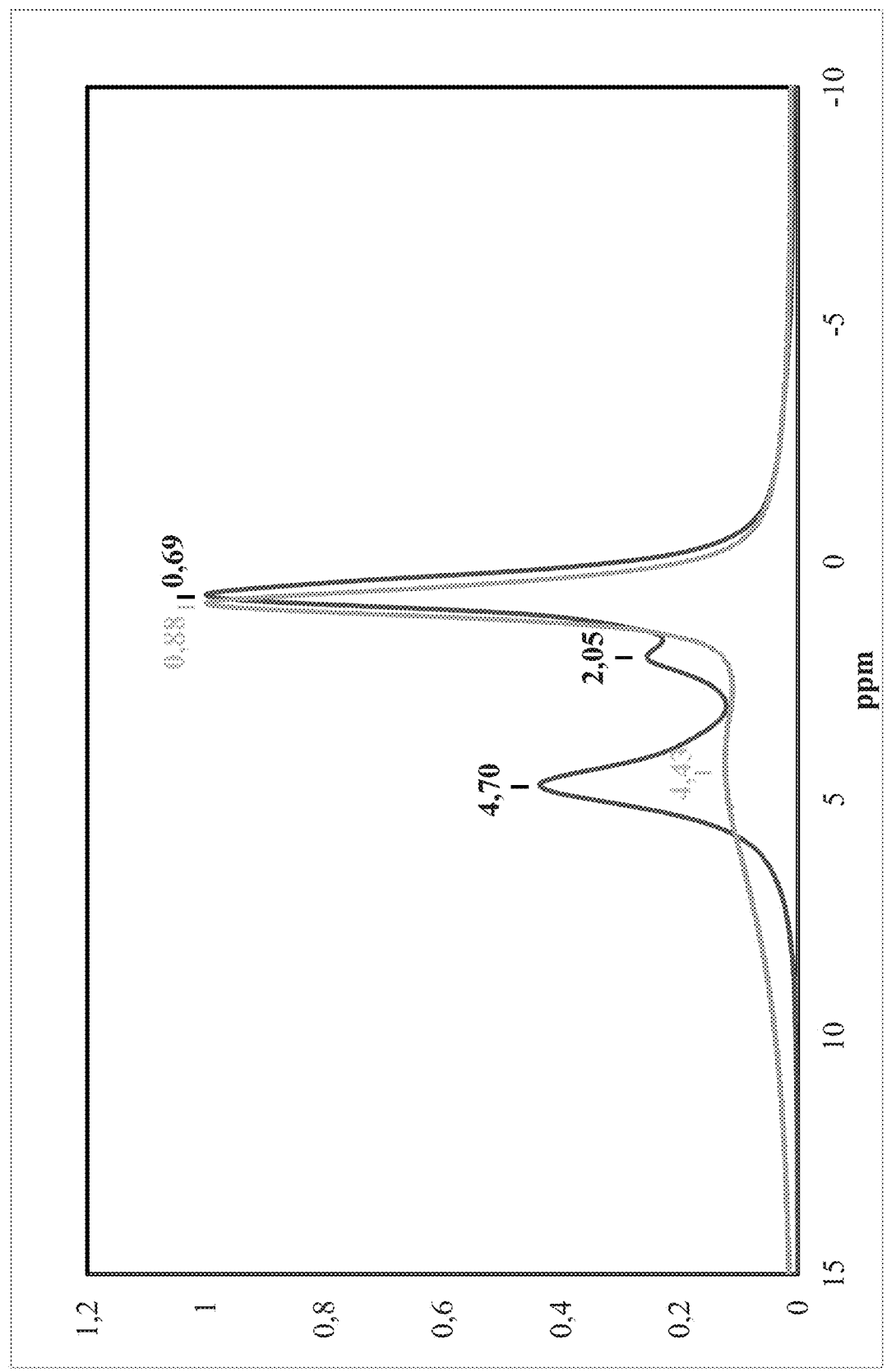

FIG. 3: $^1$H NMR spectrum of synthetic talc (dark gray) and the hybrid "synthetic talc-red wine" (light gray). The normalized intensity is represented on the ordinates. The peaks of water physisorbed at 4.70 ppm and 4.43 ppm, the silanol functions at 2.05 ppm and the structural H at 0.69 ppm and 0.88 ppm are noted.

FIG. 4: Schematic view of a device for implementing a method for preparing a synthetic phyllosilicate in which the solvothermal treatment is carried out continuously.

EXPERIMENTAL PART

I—Material and Methods
I.A. Equipment
Purple crystal: commercially available from Aldrich under the reference C6158-50G
Malachite green: commercially available from Aldrich under the reference M9015-25G
Red wine: available commercially from the company "Domaine Py" under the reference" Merlot old vines", bottle of 75 cl vintage 2014.
Natural talc: it comes from the Trimouns quarry in Luzenac in the Pyrenees Ariège, France. It was manually picked by on-site selection of the best possible grade of ore, from the point of view of mineralogical purity (2:99% talc).
Synthetic nanoscale talc: it was manufactured according to the protocol described in Example 1 of Application WO2013/004979.
Nanoscale synthetic kaolinite:
A solution of aluminum nitrate is prepared with 37.51 g (0.1 mole) of aluminum nitrate nonahydrate in 200 ml of pure water.
A solution of potassium metasilicate is also prepared from 29.67 g of an aqueous solution of potassium metasilicate ($K_2SiO_3$) having a solids content of 52% (i.e. 0.1 mole of potassium metasilicate), of 100 ml 1 M potassium hydroxide (KOH) and 200 mL of pure water.
The first solution of aluminum nitrate is added with stirring to the potassium metasilicate solution and a white precipitate is formed instantly.
The resulting suspension is stirred for 5 minutes. Three washing cycles are then carried out with distilled water and centrifugation at 8000 rpm for 10 minutes at each new centrifugation. These successive washes with elimination of the supernatant solution after each centrifugation make it possible to eliminate the potassium nitrate formed during the precipitation reaction of the precursor gel. The precursor gel placed in a closed titanium reactor placed in an oven is then subjected to a hydrothermal treatment at a temperature of 300° C. for 24 hours under the saturated vapor pressure of the water in the reactor. After cooling to room temperature, the reactor is opened and the suspension obtained is centrifuged. After centrifugation, a composition comprising particles of compound of formula $Al_2Si_2O_5(OH)_4$ is recovered. The composition of particles recovered after centrifugation is dried in an oven (120° C., 12 hours) and then ground with a mortar. The composition obtained is in the form of a white powder.

The X-ray diffractogram of this composition has the following characteristic diffraction lines:
a plane (001) located at a distance of 7.15 Å;
a plane (020) located at a distance of 4.46 Å;
a plane (110) located at a distance of 4.37 Å;
a plane (111) located at a distance of 4.16 Å;
a plane (021) located at a distance of 3.80 Å;
a plane (002) located at a distance of 3.56 Å;
a plane (130) and a plane (201) located at a distance of 2.56 Å
a plane (131) and a plane (200) located at a distance of 2.50 Å;
a plane (202) and a plane (131) located at a distance of 2.33 Å;
a plane (060), a plane (331) and a plane (331) located at a distance of 1.49 Å.

The mid-infrared spectrum of the synthetic kaolinite composition obtained has four 3620 $cm^{-1}$, 3651 $cm^{-1}$, 3667 $cm^{-1}$ and 3693 $cm^{-1}$ vibration bands representative of the hydroxyl group elongation vibrations (OH) synthetic kaolinite.

Synthetic Nanoscale Mica:
300 ml of an aqueous solution of magnesium sulphate (33.27 g or 0.135 mol) and sulfuric acid (120 g of a 0.5 M solution) are prepared.
A solution of potassium metasilicate is then prepared by diluting 59.35 g (ie 0.2 mol) of an aqueous solution of potassium metasilicate ($K_2SiO_3$) containing 52% solids in 150 ml of demineralized water. This solution of potassium metasilicate is added to the previous solution and a white precipitate is formed instantly.
The resulting suspension is stirred for 5 minutes. Three washing cycles are then carried out with distilled water and centrifugation at 8000 rpm for 10 minutes at each new centrifugation. These successive washes with elimination of the supernatant solution ante after each centrifugation make it possible to eliminate the potassium sulphate formed during the precipitation reaction of the precursor gel. Finally, the recovered white precipitate is suspended in demineralized water to a final volume of 500 ml and subjected to ultrasound with magnetic stirring for 10 minutes until a homogeneous suspension of white color is obtained. precursor gel.
988 mg of hydrated potassium hydroxide (containing 85% of potassium hydroxide and 15% of water, i.e. 0.015 mole of added pure potassium hydroxide), previously diluted in 30 ml of demineralized water, are then added to the precursor gel, and the suspension obtained is stirred magnetically. for 5 minutes at room temperature (22.5° C.).
The precursor gel placed in a closed titanium reactor placed in an oven is then subjected to a hydrothermal treatment at a temperature of 300° C. for 24 hours under the saturated vapor pressure of the water in the reactor.
After cooling to room temperature, the reactor is opened and the suspension obtained is centrifuged. After centrifugation, a composition comprising at least 80% by weight of particles of formula $K_{0.3}$ $Si_4$ $Mg_{2.7}$ $O_{10}$ $(OH)_2$ is recovered.
The composition of particles recovered after centrifugation is dried in an oven for 12 hours at 120° C. and then ground in a mortar. The composition obtained is in the form of a white powder.
The X-ray diffractogram of the composition of particles of formula $K_{0.3}$ $Si_4$ $Mg_{2.7}$ $O_{10}$ $(OH)_2$ thus obtained has the following characteristic diffraction lines:

a plane (001) located at a distance of 10.15 Å;
a plane (002) located at a distance of 5.03 Å;
a plane (020) located at a distance of 4.53 Å;
(003) and (022) planes located at a distance of 3.34 Å;
a plane (131) located at a distance of 2.60 Å;
a plane (005) located at a distance of 2.01 Å;
a plane (060) located at a distance of 1.52 Å.

The composition is then subjected to an anhydrous heat treatment at 550° C. in an oven for 5 hours. The composition obtained after the anhydrous heat treatment remains white.

The X-ray diffractogram of the composition of particles of formula $K_{0.3}\ Si_4\ Mg_{2.7}\ O_{10}\ (OH)_2$ obtained after an anhydrous heat treatment at 550° C. has, after the anhydrous heat treatment, the following characteristic diffraction lines:
a plane (001) located at a distance of 10.24 Å;
a plane (002) located at a distance of 5.02 Å;
a plane (020) located at a distance of 4.56 Å;
(003) and (022) planes located at a distance of 3.37 Å;
a plane (131) located at a distance of 2.60 Å;
a plane (005) located at a distance of 2.02 Å;
a plane (060) located at a distance of 1.52 Å.

I.B. Methods
I.B.1. Syntheses

Example 1: Synthesis of the Hybrid Nanomaterial Composition Based on Synthetic Talc and Red Wine 40 milliliters of red wine are added at room temperature to a suspension of 1 g of nanotalc in 100 ml of pure water. The pink suspension is stirred under sonication for 5 minutes and then centrifuged at 14000 rpm for 20 min. It is noted that the supernatant is slightly colored which reflects the partial adsorption of the dyes of the wine on the mineral. The base consists of a pink paste. This paste can be dried in an oven (60° C. for 12 h) or by freeze drying or any other drying technique.

Example 2: Synthesis of the Hybrid Nanomaterial Composition Based on Synthetic Kaolinite and Red Wine The same protocol was applied as in Example 1, using the synthetic kaolinite whose preparation is detailed above.

Example 3: Synthesis of the Hybrid Nanomaterial Composition Based on Synthetic Mica and Red Wine The same protocol was applied as in Example 1, using the synthetic mica whose preparation is detailed above.

I.B.2. Tests
Characterization—Test No. 1: Adsorption Test:
a) General Protocol

In order to demonstrate the high adsorptivity of synthetic minerals and the way in which organic molecules interact with talc, various adsorption tests have been carried out. In a beaker, a mineral in the form of an aqueous suspension is mixed with a dye dissolved in a solvent. If necessary, water is added so that the mixture is sufficiently liquid. The whole is then stirred and passed under ultrasound until the mixture is homogeneous and without visible agglomerate. The final step is to centrifuge the mixture at 9000 rpm for about 20 minutes. At the end of this, the mineral is found plated in the bottom of the pot surmounted by the supernatant. Therefore, if the mineral has completely adsorbed the dye, it is colored in the bottom of the pot and the supernatant is colorless and clear. On the contrary, if it has not adsorbed the dye, the mineral retains its initial color and the supernatant is colored. If at the end of this first centrifugation the supernatant is colored and the mineral is too, it means that the mineral has not adsorbed all the dye. The supernatant is then replaced by deionized water in the pot for a second centrifugation. This operation makes it possible to see whether the adsorption is strong or whether the mineral rejects the dye (leaching). This centrifugation step is performed as many times as necessary.

b) Comparison Test of the Adsorbent Capacity of Natural and Synthetic Talc

First of all, adsorption tests were carried out to compare the adsorbent capacity of synthetic talc with that of natural talc. For this, different organic dyes have been chosen, namely crystal violet, malachite green, red wine. The latter were brought into contact with synthetic talc or natural talc in the same ratio of "amount of dye/amount of mineral" for a better comparison of the results. At the end of the centrifugation, the color of the minerals and the supernatant are compared to evaluate the adsorbent capacity of the mineral.

These dyes were chosen because they all have a positive or negative surface charge.

Different tests having been carried out with uncharged dyes (β-carotene, curcumin, not reported here) have shown negative results in the adsorption test on synthetic talc.

Characterization—Tests No. 2: Characterization Methods
a) X-Ray Diffraction

The XRD analyzes were carried out on a D2 Phaser type apparatus from the Bruker company, with a wavelength of 1.54060 (λcu), over a diffraction angle range of from 0 to 80°2θ. Moreover, the study of diffractograms made it possible to determine the coherence range of the mineral, ie the number of TOT sheets stacked along the c * axis without any major flaws. This coherence domain was calculated using Scherrer's formula:

$$L = \frac{0.91 \times \lambda}{B \times \cos(\theta)}$$

where L corresponds to the size of the coherent domain (λ), to the B×cos (θ) the wavelength of the radiation, B to the width of the peak at half-height (rad), and θ the angle of the diffraction line.

b) Granulometry

The measurements of the particle size of the synthetic talc were carried out with a Vasco-2 granulometer of Cordouan Technologies, specific for the detection of nanoparticles. The analysis results correspond to a statistical study comprising 20 measurements with an acquisition time of one minute per measurement.

c) Nuclear Magnetic Resonance of the $^1H$ $^1H$ NMR analysis was performed using a Bruker Avance 400 spectrometer equipped with a 4 mm probe operating at 399.60 MHz for the proton $^1H$.

f) Carbon Analyzer

Finally, a carbon analyzer was used to measure the amount of carbon adsorbed on the nanoparticles of synthetic talc during adsorption tests (for the same ratio of "amount of dye/amount of mineral"). The measurements were performed on a HORIBA-Carbon/Sulfur analyzer apparatus of the EMIA-320V model. The sample is placed in a crucible which is heated for 110 seconds in an oven with a temperature ramp from 0 to 1500° C. During this heating, the sample is vaporized and transforms into gas (including $CO_2$). An infrared detector then measures the percentage of carbon from the sample. During handling, the NCS HC16024 standard containing 3.59% C was passed in and out of analysis to validate the results.

I.B. Results

I.B.1 Results of Adsorption Tests a) Adsorbent Capacity of Synthetic Talc

The results of the adsorption tests of natural talc and synthetic talc are the following: In all cases, it is noted that after switching to the centrifuge, the mixture which was homogeneous and colored as a whole has two distinct phases: a precipitate of colored talcum at the bottom of the pot and a more or less colored supernatant. In the case of natural talc, the supernatant is each time a little colored, which means that the mineral has not totally adsorbed the dye. In contrast, in the case of synthetic talc, the supernatant is each time perfectly colorless and limpid which means that the mineral has completely adsorbed the dye. An exception comes from the wine test where the synthetic talc does not adsorb all the compounds but only a part of the dyes of the wine.

I.B.2. Characterization of the Interaction "Synthetic Talc—Red Wine"

a) XRD

In the presence of red wine, the talc (001) line shifts towards small angles, thus marking an increase in the inter-reticular distance between the layers (FIG. 1). It would seem, therefore, that red wine dyes (anthocyanins) also adsorb on the basal surfaces of talc.

b) Granulometry

Following the adsorption of anthocyanins in red wine, the two populations of talc particles with an average size of 45 nm and 259 nm increase in size to 65 nm and 543 nm (FIG. 2) due to probable agglomeration. particles due to the interaction of anthocyanins with each other.

c) NMR

The $^1$H NMR results on the hybrid "synthetic talc—red wine" (FIG. 3) show that, in the presence of anthocyanins in the system, the NMR spectrum does not exhibit the characteristic peak of the silanol functions Si—OH centered at 2.05 ppm.

This would indicate that the dye interacted with these functions which modified the chemical environment around the hydrogen atom.

d) Carbon Analysis

Finally, a carbon analysis was performed to compare the amount of dye that was adsorbed between synthetic talc and natural talc during adsorption tests. The analysis results were validated by the NCS HC16024 standard containing 3.59%. Table 1 below shows the results obtained.

TABLE 1

|  | Natural talc + wine | Synthetic talc + wine | NCS HC16024 "entry" | NCS HC16024 "exit" |
|---|---|---|---|---|
| % C | 0.8304 | 4.3028 | 3.61 | 3.55 |

These results show that synthetic talc adsorbed about 5 times more dyes than natural talc. This analysis therefore highlights the strong adsorption power of the synthetic mineral.

The invention claimed is:

1. A method for preparing an organic/inorganic hybrid composition comprising non-swelling phyllosilicate nanoparticles having a thickness of 1 nm to 100 nm, and a largest dimension of 10 nm to 10 µm, and at least one molecule chosen from colored charged organic molecules, said organic molecule being adsorbed on the phyllosilicate nanoparticles, this method comprising at least bringing into contact, in a monophasic solvent medium, said at least one colored charged organic molecule with said non-swelling phyllosilicate nanoparticles.

2. The method according to claim 1, which comprises at least the following steps:
   (i) providing a solution (a) of at least one colored charged organic molecule in at least one solvent,
   (ii) providing a suspension (b) of non-swelling phyllosilicate nanoparticles in at least one solvent, and
   (iii) contacting the solution (a) and the suspension (b), the non-swelling phyllosilicate nanoparticles having a thickness of 1 nm to 100 nm, and a largest dimension of 10 nm to 10 µm.

3. The method according to claim 2 wherein the non-swelling phyllosilicates have one of the following chemical formulas:

$$(Si_xGe_{(1-x)})_4M_3O_{10}(OH)_2, \quad \text{(I) in which:}$$

x is a real number of the interval [0; 1], and

M denotes at least one divalent metal having the formula $Mg_{y1}Co_{y2}Zn_{y3}Cu_{y4}Mn_{y5}Fe_{y6}Ni_{y7}Cr_{y8}$; each index y1, y2, y3, y4, y5, y6, y7 and y8 representing a real number of the interval [0; 1], and such that $\Sigma_{i=1}^{8} yi=1$, or $$(Al_{y'}M'_{(1-y')})_2(Si_{x'}Ge_{(1-x')})_2O_5(OH)_4, \quad \text{(II) in which:}$$

M' denotes at least one trivalent metal chosen from the group formed of gallium and rare earths, y' is a real number of the interval [0; 1], and x' is a real number of the interval [0; 1], or $$A_t(Si_{x''}Ge_{(1-x'')})_4M''_kO_{10}(OH)_2, \quad \text{(III) in which:}$$

A denotes at least one monovalent cation of a metal element having the formula $Li_{w1}Na_{w2}K_{w3}Rb_{w4}Cs_{w5}$, each w1, w2, w3, w4 and w5 representing a real number of the interval [0; 1] such that $\Sigma_{i=1}^{5} wi=1$, x'' is a real number of the interval [0; 1], M'' denotes at least one divalent metal having the formula $Mg_{j1}Co_{j2}Zn_{j3}Cu_{j4}Mn_{j5}Fe_{j6}Ni_{j7}Cr_{j8}$; each index j1, j2, j3, j4, j5, j6, j7 and j8 representing a real number of the interval [0; 1], and such that $\Sigma_{i=1}^{8} ji=1$, k is a real number in the range [2.50; 2.85], and t+2 k is a real number of the interval [5.3; 6.0].

4. The method according to claim 2, in which the colored organic molecule is selected in the group consisting of:
   polyphenols,
   methylene blue, crystal violet, congo red, porphyrins, eosin Y, eosin B, thiazole orange, acid black 1, acid black 2, eriochrome black T, patent blue V,
   an aqueous extract of a colored vegetable fraction,
   an aqueous extract of a colored animal fraction,
   a product derived from an aqueous extract of a colored vegetable fraction or an aqueous extract of a colored animal fraction, and
   mixtures of these colored organic molecules.

5. A hybrid nanoparticle composition comprising at least one non-swelling phyllosilicate and at least one molecule chosen from colored charged organic molecules, said organic molecule being adsorbed on the phyllosilicate, this composition being obtained by the method according to claim 2.

6. The method according to claim 1, in which the colored organic molecule is selected in the group consisting of:
polyphenols,
methylene blue, crystal violet, congo red, porphyrins, eosin Y, eosin B, thiazole orange, acid black 1, acid black 2, eriochrome black T, patent blue V,
an aqueous extract of a colored vegetable fraction,
an aqueous extract of a colored animal fraction,
a product derived from an aqueous extract of a colored vegetable fraction or an aqueous extract of a colored animal fraction, and
mixtures of these colored organic molecules.

7. The method according to claim 1 wherein the non-swelling phyllosilicates have one of the following chemical formulas:

$$(Si_xGe_{(1-x)})_4M_3O_{10}(OH)_2, \quad \text{(I) in which:}$$

x is a real number of the interval [0; 1], and
M denotes at least one divalent metal having the formula $Mg_{y1}Co_{y2}Zn_{y3}Cu_{y4}Mn_{y5}Fe_{y6}Ni_{y7}Cr_{y8}$; each index y1, y2, y3, y4, y5, y6, y7 and y8 representing a real number of the interval [0; 1], and such that $\Sigma_{i=1}^{8} i=yi=1$,
or $$(Al_{y'}M'_{(1-y')})_2(Si_{x'}Ge_{(1-x')})_2O_5(OH)_4, \quad \text{(II) in which:}$$

M' denotes at least one trivalent metal chosen from the group formed of gallium and rare earths,
y' is a real number of the interval [0; 1], and
x' is a real number of the interval [0; 1],
or $$A_t(Si_{x''}Ge_{(1-x'')})_4M''_kO_{10}(OH)_2, \quad \text{(III) in which:}$$

A denotes at least one monovalent cation of a metal element having the formula $Li_{w1}Na_{w2}K_{w3}Rb_{w4}Cs_{w5}$ each w1, w2, w3, w4 and w5 representing a real number of the interval [0; 1] such that $\Sigma_{i=1}^{5} wi=1$,
x'' is a real number of the interval [0; 1],
M'' denotes at least one divalent metal having the formula $Mg_{j1}Co_{j2}Zn_{j3}Cu_{j4}Mn_{j5}Fe_{j6}Ni_{j7}Cr_{j8}$; each index j1, j2, j3, j4, j5, j6, j7 and j8 representing a real number of the interval [0; 1], and such that $\Sigma_{i=1}^{8} ji=1$,
k is a real number in the range [2.50; 2.85], and
t+2 k is a real number of the interval [5.3; 6.0].

8. The method according to claim 7, in which the colored organic molecule is selected in the group consisting of:
polyphenols,
methylene blue, crystal violet, congo red, porphyrins, eosin Y, thiazole orange, acid black 1, acid black 2, eriochrome black T, patent blue V,
an aqueous extract of a colored vegetable fraction,
an aqueous extract of a colored animal fraction,
a product derived from an aqueous extract of a colored vegetable fraction or an aqueous extract of a colored animal fraction, and
mixtures of these colored organic molecules.

9. The method according to claim 7, in which the non-swelling phyllosilicates are formed of a stack of elementary sheets:
of 2:1 phyllosilicate and of chemical formula $Si_4M_3O_{10}(OH)_2$,
or
of 1:1 phyllosilicate and of chemical formula $Al_2Si_2O_5(OH)_4$,
or
of 2:1 phyllosilicate and of chemical formula $K Si_4 Mg_{2.5}O_{10}(OH)_2$ (IIId) or $K_{0.8} Si_4 Mg_{26}O_{10}(OH)_2$ (IIIf).

10. The method according to claim 9, in which the colored organic molecule is selected in the group consisting of:
polyphenols,
methylene blue, crystal violet, congo red, porphyrins, eosin Y, eosin B, thiazole orange, acid black 1, acid black 2, eriochrome black T, patent blue V,
an aqueous extract of a colored vegetable fraction,
an aqueous extract of a colored animal fraction,
a product derived from an aqueous extract of a colored vegetable fraction or an aqueous extract of a colored animal fraction, and
mixtures of these colored organic molecules.

11. The method according to claim 9, in which the non-swelling phyllosilicates are formed of a stack of elementary sheets of 2:1 phyllosilicate and of chemical formula $Si_4Mg_3O_{10}(OH)_2$.

12. An organic/inorganic hybrid nanoparticle composition comprising at least one non-swelling phyllosilicate having a thickness of 1 nm to 100 nm, and a largest dimension of 10 nm to 10 μm and at least one molecule chosen from colored charged organic molecules, said organic molecule being adsorbed on the phyllosilicate.

13. The composition according to claim 12, wherein the ratio of organic colored molecule/phyllosilicate is from 0.01% of carbon to 5% of carbon, mass of carbon relative to the mass of phyllosilicate.

14. A method for preparing organic/inorganic hybrid nanoparticles comprising at least one non-swelling phyllosilicate having a thickness of 1 nm to 100 nm, and a largest dimension of 10 nm to 10 μm and at least one molecule chosen from colored charged organic molecules, said organic molecule being adsorbed on the non-swelling phyllosilicate, said method comprising the following steps:
bringing into contact, in a monophasic solvent medium, said at least one molecule chosen from colored charged organic molecules with said non-swelling phyllosilicate nanoparticles,
elimination of the solvent phase, and
recovery of nanoparticles.

15. The method according to claim 14, wherein the non-swelling phyllosilicates have one of the following chemical formulas:

$$(Si_xGe_{(1-x)})_4M_3O_{10}(OH)_2, \quad \text{(I) in which:}$$

x is a real number of the interval [0; 1], and
M denotes at least one divalent metal having the formula $Mg_{y1}Co_{y2}Zn_{y3}Cu_{y4}Mn_{y5}Fe_{y6}Ni_{y7}Cr_{y8}$; each index y1, y2, y3, y4, y5, y6, y7 and y8 representing a real number of the interval [0; 1], and such that $\Sigma_{i=1}^{8} yi=1$,
or $$(Al_{y'}M'_{(1-y')})_2(Si_{x'}Ge_{(1-x')})_2O_5(OH)_4, \quad \text{(II) in which:}$$

M' denotes at least one trivalent metal chosen from the group formed of gallium
and rare earths,
y' is a real number of the interval [0; 1], and
x' is a real number of the interval [0; 1],
or $$A_t(Si_{x''}Ge_{(1-x'')})_4M''_kO_{10}(OH)_2, \quad \text{(III) in which:}$$

A denotes at least one monovalent cation of a metal element having the formula $Li_{w1}Na_{w2}K_{w3}Rb_{w4}Cs_{w5}$, each w1, w2, w3, w4 and w5 representing a real number of the interval [0; 1] such that $\Sigma i=1^{5} wi=1$,
x'' is a real number of the interval [0; 1], M" denotes at least one divalent metal having the formula $Mg_{j1}Co_{j2}Zn_{j3}Cu_{j4}Mn_{j5}Fe_{j6}Ni_{j7}Cr_{j8}$; each index j1, j2, j3, j4, j5, j6, j7 and j8 representing a real number of the interval [0; 1], and such that $\Sigma_{i=1}^{8} ji=1$, k is a real number in the range [2.50; 2.85], and t+2 k is a real number of the interval [5.3; 6.0].

16. The method according to claim 14, in which the colored organic molecule is selected in the group consisting of:

polyphenols, methylene blue, crystal violet, congo red, porphyrins, eosin Y, eosin B, thiazole orange, acid black 1, acid black 2, eriochrome black T, patent blue V, an aqueous extract of a colored vegetable fraction, an aqueous extract of a colored animal fraction, a product derived from an aqueous extract of a colored vegetable fraction or an aqueous extract of a colored animal fraction, and mixtures of these colored organic molecules.

17. A hybrid nanoparticle composition comprising at least one non-swelling phyllosilicate and at least one molecule chosen from colored charged organic molecules, said organic molecule being adsorbed on the phyllosilicate, this composition being obtained by the method according to claim 14.

\* \* \* \* \*